United States Patent [19]

Ueda

[11] Patent Number: 4,988,596

[45] Date of Patent: Jan. 29, 1991

[54] PHOTOSENSITIVE MEMBER CONTAINING HYDRAZONE COMPOUND WITH STYRYL STRUCTURE

[75] Inventor: Hideaki Ueda, Osaka, Japan

[73] Assignee: Minolta Camera Kabushiki Kaisha, Osaka, Japan

[21] Appl. No.: 477,461

[22] Filed: Feb. 9, 1990

[30] Foreign Application Priority Data

Feb. 10, 1989 [JP] Japan ................................ 1-31835
Feb. 10, 1989 [JP] Japan ................................ 1-31837
Feb. 10, 1989 [JP] Japan ................................ 1-31838

[51] Int. Cl.$^5$ ........................ G03G 5/05; G03G 5/14
[52] U.S. Cl. ................................ 430/59; 252/500
[58] Field of Search ........................ 430/59, 58

[56] References Cited

U.S. PATENT DOCUMENTS

| | | | |
|---|---|---|---|
| 4,150,987 | 4/1979 | Anderson et al. | 430/59 |
| 4,362,789 | 12/1982 | Anderson et al. | 430/59 |
| 4,399,208 | 8/1983 | Takasu et al. | 430/59 |
| 4,423,129 | 12/1983 | Takasu et al. | 430/59 |
| 4,462,280 | 2/1987 | Ueda | 430/59 |
| 4,465,857 | 8/1984 | Neumann et al. | 430/73 X |
| 4,477,550 | 10/1984 | Horie et al. | 430/59 |
| 4,784,929 | 11/1988 | Ueda | 430/59 |

*Primary Examiner*—David Welsh
*Attorney, Agent, or Firm*—Burns, Doane, Swecker & Mathis

[57] ABSTRACT

The present invention relates to a photosensitive member comprising
an electrically conductive substrate, and
a photosensitive layer formed on or over the substrate and including a hydrazone compound represented by the general formula (I);

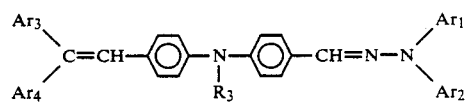

29 Claims, 1 Drawing Sheet

PHOTOSENSITIVE MEMBER CONTAINING HYDRAZONE COMPOUND WITH STYRYL STRUCTURE

BACKGROUND OF THE INVENTION

This invention relates to a photosensitive member containing a specific hydrazone compound with a styryl structure.

In electrophotography, copied images are formed by various methods. For example, the surface of a photosensitive member is charged and irradiated to form electostatic latent images thereon, the electrostatic latent images are developed to visible images by a developer, and then the developed images are fixed directly onto the photosensitive member (this method is referred to as a direct method). Alternatively, developed electrostatic latent images on a photosensitive member which are made visible by a developer are transferred to a copying paper and then, the transferred images are fixed on the paper (this method is referred to as a powder transferring method). In another method, electrostatic latent images on a photosensitive member are tranferred onto a copying paper, the transferred electrostatic latent images are developed by a developer and then fixed on the copying paper(referred to as an electrostatic latent image transferring method).

Known photosensitive materials for forming a photosensitive member as above mentioned include inorganic photoconductive materials such as selenium, cadmium sulfide or zinc oxide.

These photosensitive materials have many advantages such as low loss of charges in the dark, an electrical charge which can be rapidly dissipated with irradiation of light and the like. However, they have disadvantages. For example, a photosensitive member based on selenium is difficult to produce, has high production costs and is difficult to handle due to inadequate resistivity to heat or mechanical impact. A photosensitive member based on cadmium sulfide or zinc oxide has defects such as its unstable sensitivity in a highly humid environment and loss of stability with time because of the deterioration of dyestuffs, added as a sensitizer, by corona charge and fading with exposure.

Many kinds of organic photoconductive polymers such as polyvinylcarbazole and so on have been proposed. These organic photoconductive polymers have superior film forming properties, are light in weight, etc., but inferior in sensitivity, durability and environmental stability compared to the aforementioned inorganic photoconductive materials.

Physical properties or electrophotographic properties of a coating layer as a photosensitive member may be adjusted desirably by using an organic photoconductive material of low molecular weight in the combination with a selected binder resin, a selected composition or the like. However, the high mutual solubility of an organic photoconductive material with a binder resin is required because the photoconductive material is used together with the binder resin.

A photosensitive member prepared by dispersing an organic photoconductive compound of low molecular weight or high molecular weight in a binder resin has problems such as high residual potential caused by many traps of carriers, low sensitivity and the like. Therefore, a charge transporting material is further incorporated in a photosensitive member in order to overcome the problems as above mentioned, and a function-divided photosensitive member of a laminated or a dispersed type has been also proposed, in which charge generating function and charge transporting function are divided by different layers or different dispersed materials.

Many kinds of organic compounds are used as a charge transporting material, which have, however, many problems. For example, 2,5-bis(p-diethylaminophenyl)-1,3,4-oxadiazole disclosed in U.S. Pat. No.3,189,447 is low in compatibility with a binder and liable to separate out. A diarylalkane derivative disclosed in U.S. Pat. No.3,820,989 is good in mutual solubility with a binder resin, but changes in sensitivity when used repeatedly. A hydrazone compound disclosed in JP Laid-open No. 54-59143 is relatively good in residual potential properties, but being poor in chageability and repetition properties.

In practice, there are few organic compounds suitable for the preparation of a photosensitive member as above mentioned.

SUMMARY OF THE INVENTION

The object of the invention is to provide a photosensitive member excellent in sensitivity, chageability, fatigue properties when used repeatedly, stability in electrophotographic properties by incorporating a specified hydrazone compound with excellent mutual solubility with a binder resin and excellent charge transportability.

This invention relates to a photosensitive member comprising an electrically conductive substrate; and a photosensitive layer formed on or over the substrate and including a hydrazone compound represented by the general formula (I);

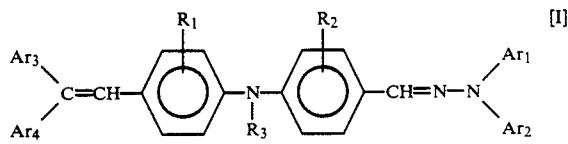

wherein $R_1$ and $R_2$ are independently a hydrogen atom, an alkyl group, an alkoxy group or a halogen atom; $R_3$ is a hydrogen atom, an alkyl group which may have a substituent, an aralkyl group which may have a substituent, an aryl group which may have a substituent, a condensed polycyclic ring group which may have a substituent or a heterocyclic ring group which may have a substituent; $R_3$ may form a condensed ring group together with a benzene ring in the formula (I); $Ar_1$ and $Ar_2$ are independently an alkyl group which may have a substituent, an aryl group which may have a substituent, a condensed polycyclic ring group which may have a substituent or a heterocyclic ring group which may have a substituent; $Ar_3$ and $Ar_4$ are independently a hydrogen atom, an alkyl group which may have a substituent, an aryl group which may have a substituent, a condensed polycyclic ring group which may have a substituent or a heterocyclic ring group which may have a substituent; $Ar_3$ and $Ar_4$ are not hydrogen atoms at the same time; $Ar_1$ and $Ar_2$, and/or $Ar_3$ and $Ar_4$ may form a ring in combination.

DETAILED DESCRIPTION OF THE INVENTION

Figure 1:
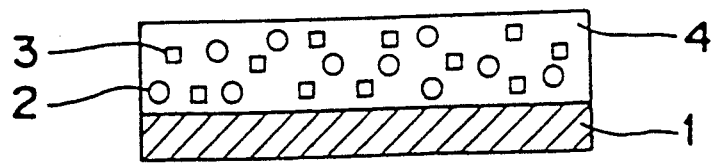
FIG. 1 is a diagram showing the structure of a dispersion-type photosensitive member embodying the invention comprising a photosensitive layer formed on an electrically conductive substrate.

The present invention provides a photosensitive member excellent in sensitivity, charge transportability, initial surface potential, potential reducing ratio in the dark, light-fatigue properties when used repeatedly.

The present invention has accomplished the above object by the introduction of a specific hydrazone compound excellent in mutual solubility with a binder resin and charge transportability into a photosensitive member as a charge transporting material.

A photosensitive member provided according to the present invention contains a specific hydrazone compound represented by the following formula (I);

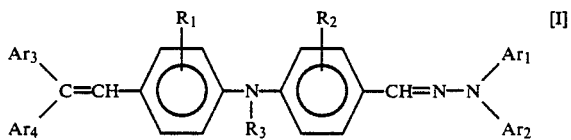

wherein $R_1$ and $R_2$ are independently a hydrogen atom, an alkyl group, an alkoxy group or a halogen atom; $R_3$ is a hydrogen atom, an alkyl group which may have a substituent, an aralkyl group which may have a substituent, an aryl group which may have a substituent, a condensed polycyclic ring group which may have a substituent or a heterocyclic ring group which may have a substituent; $R_3$ may form a condensed ring group together with a benzene ring in the formula (I); $Ar_1$ and $Ar_2$ are independently an alkyl group which may have a substituent, an aryl group which may have a substituent, a condensed polycyclic ring which may have a substituent or a heterocyclic ring group which may have a substituent; $Ar_3$ and $Ar_4$ are independently a hydrogen atom, an alkyl group which may have a substituent, an aryl group which may have a substituent, a condensed polycyclic ring group which may have a substituent or a heterocyclic ring group which may have a substituent. $Ar_3$ and $Ar_4$ are not hydrogen atoms at the same time; $Ar_1$ and $Ar_2$, and/or $Ar_3$ and $Ar_4$ may form a ring in combination.

A hydrazone compound represented by the general formula (I) has both a hydrazone structure and a styryl structure. The hydrazone structure is effective for resistance to ozone and the styryl structure is effective for sensitivity. A hydrazone compound of the present invention is excellent in both resistance to ozone and sensitivity. A simple mixture of a compound having a hydrazone structure with a compound having a styryl structure does not achieve both effects as above mentioned. Further, a hydrazone compound represented by the general formula (I) has a structure below;

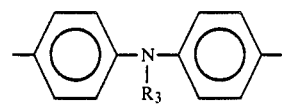

wherein $R_3$ is the same as that of the general formula (I), which is also effective for sensitivity.

$Ar_1$, $Ar_2$, $Ar_3$ and $Ar_4$ are independently an alkyl group which may have a substituent, an aryl group which may have a substituent, a condensed polycyclic ring which may have a substituent or a heterocyclic ring group which may have a substituent.

Either $Ar_3$ or $Ar_4$ may be a hydrogen atom, but both $Ar_3$ and $Ar_4$ are not hydrogen atoms at the same time.

An electron donating group is preferable for $Ar_1$, $Ar_2$, $Ar_3$ and $Ar_4$. More preferably, $Ar_3$ and $Ar_4$ are phenyl groups at the same time.

$Ar_1$ and $Ar_2$, and/or $Ar_3$ and $Ar_4$ may form a ring in combination such as carbazole and the like.

$Ar_1$, $Ar_2$, $Ar_3$ and $Ar_4$ may have a substituent respectively. A preferable substituent is an electron donating one, for example, a substituted amino group, an alkoxy group such as a methoxy group, an ethoxy group or the like. Preferable $Ar_3$ and $Ar_4$ have a substituent as above mentioned.

$R_1$ and $R_2$ are independently a hydrogen atom, an alkyl group, an alkoxy group or a halogen atom.

$R_3$ is a hydrogen atom, an alkyl group which may have a substituent, an aralkyl group which may have a substituent, an aryl group which may have a substituent, a condensed polycyclic ring group which may have a substituent or a heterocyclic ring group which may have a substituent.

$R_3$ may form a condensed ring together with a benzene ring in the formula (I) to provide a hydrazone compound represented by the general formula (III) or (IV) below;

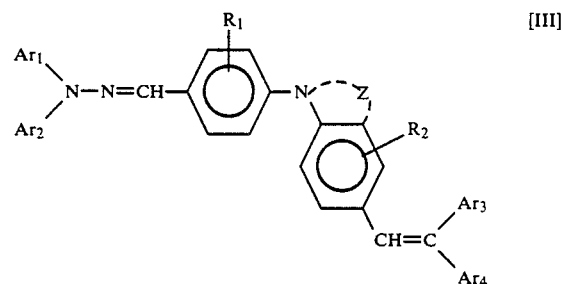

-continued

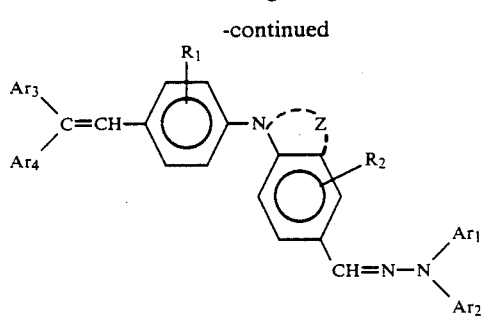
[IV]

wherein $Ar_1$-$Ar_4$, and $R_1$, $R_2$ are same as those in the general formula (I).

Examples of preferred hydrazone compounds of the present invention represented by the formula (I) are those having the following structual formula. These examples are in no way limitative. Then, a hydrazone compound represented by the general formula (III) or (IV) wherein $R_3$ forms a condensed ring in the combination with a benzene ring in the general formula (I) are shown separately.

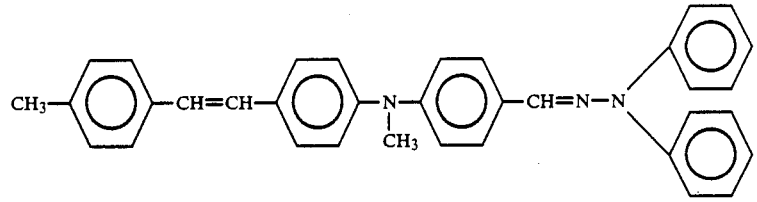
[I-1]

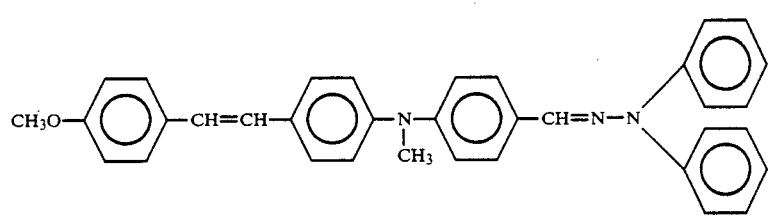
[I-2]

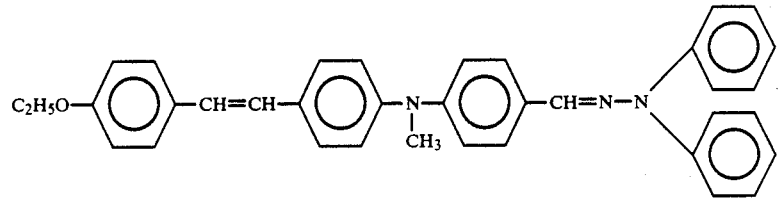
[I-3]

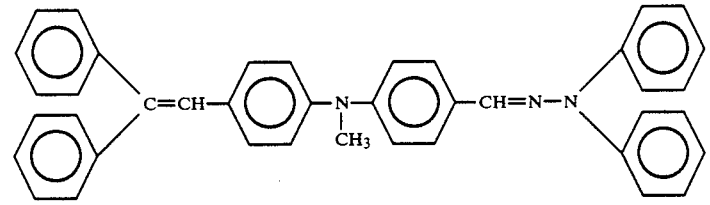
[I-4]

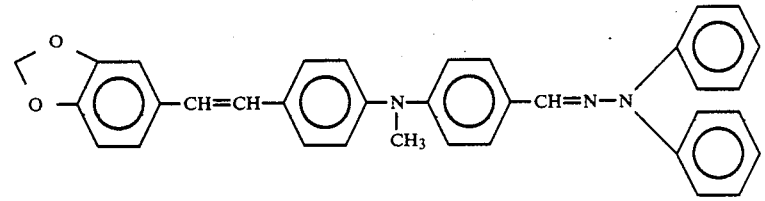
[I-5]

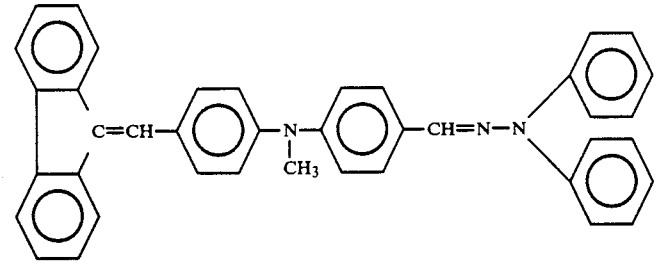
[I-6]

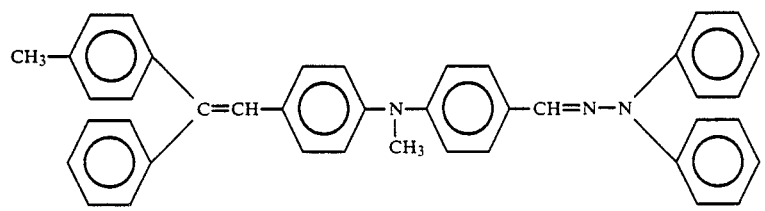
[I-7]
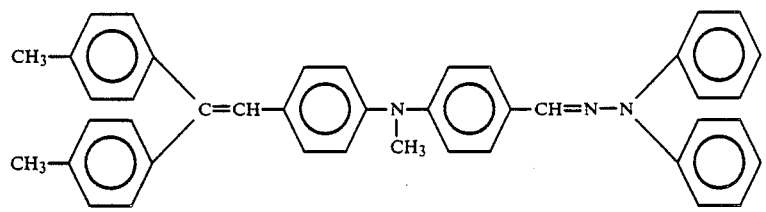
[I-8]
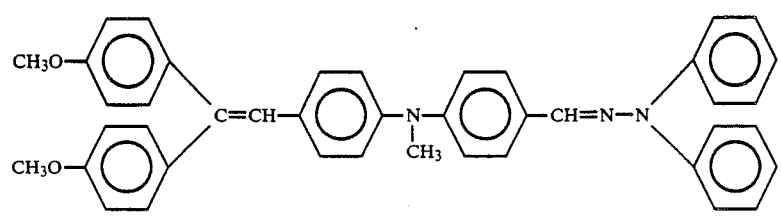
[I-9]
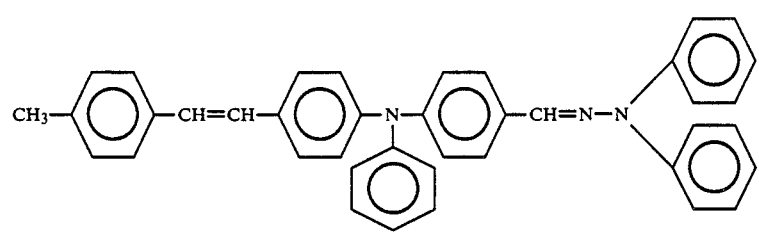
[I-10]
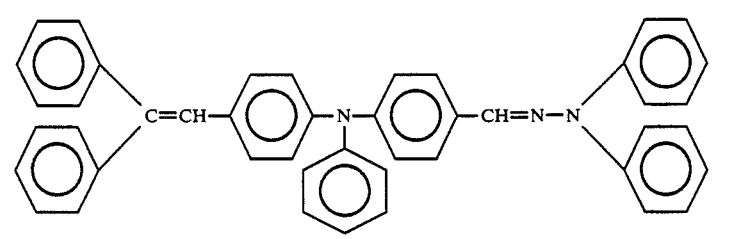
[I-11]
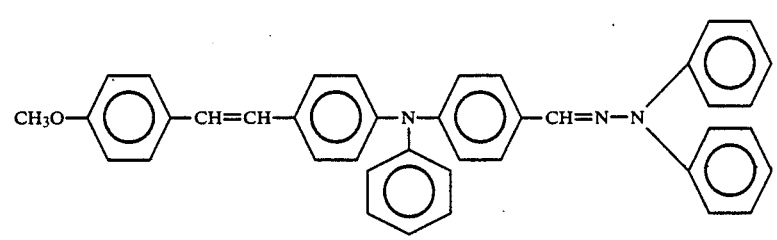
[I-12]
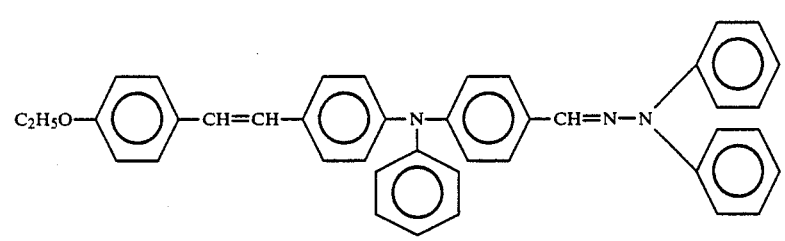
[I-13]

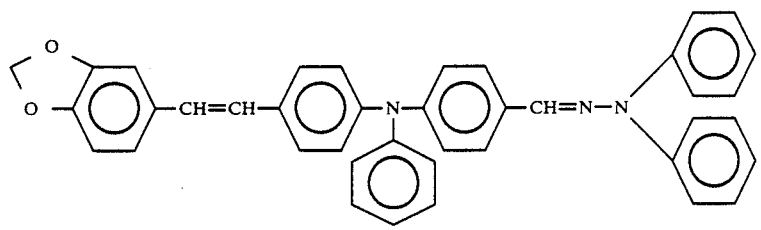
[I-14]
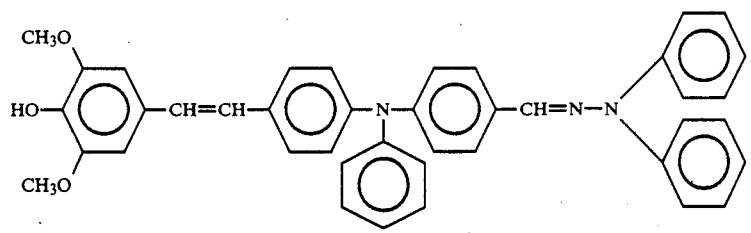
[I-15]
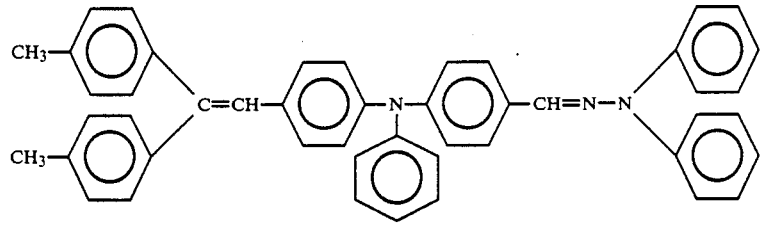
[I-16]
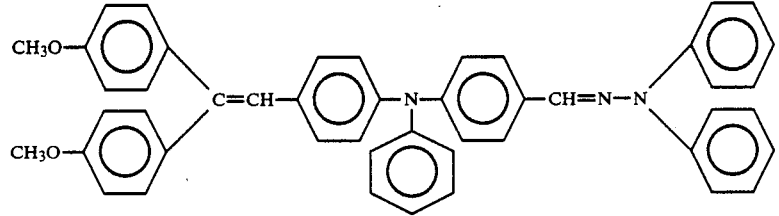
[I-17]
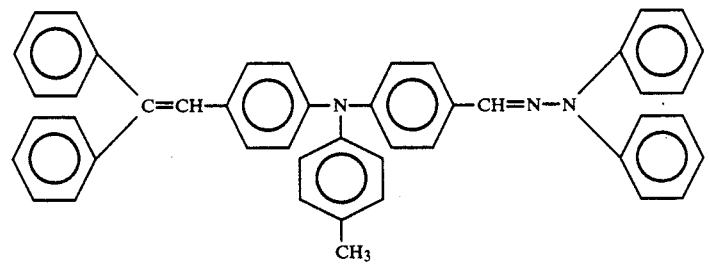
[I-18]
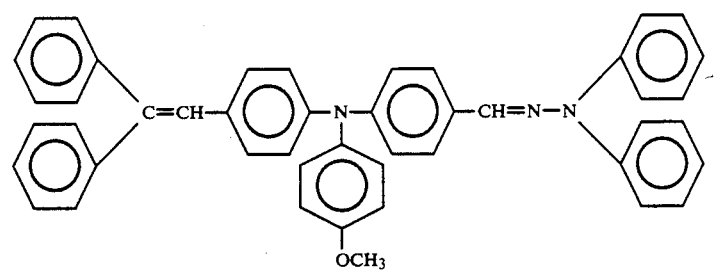
[I-19]

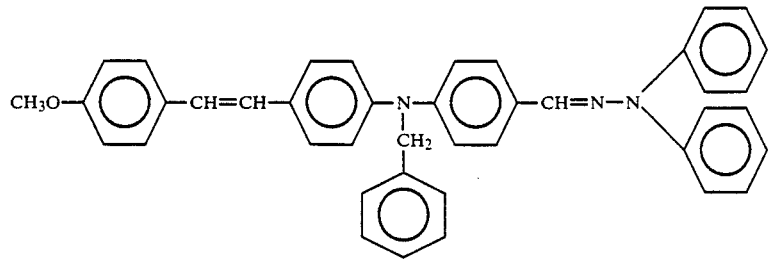
[I-20]
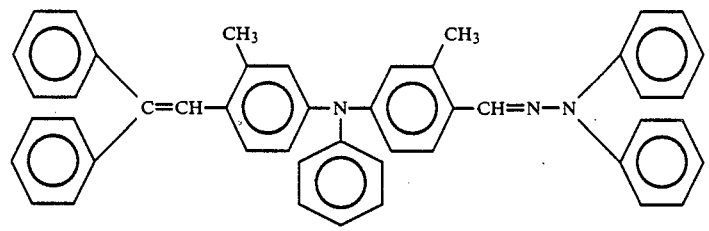
[I-21]
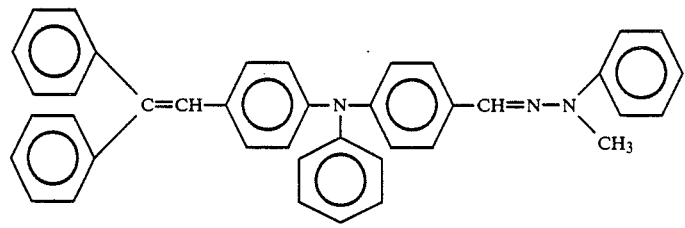
[I-22]
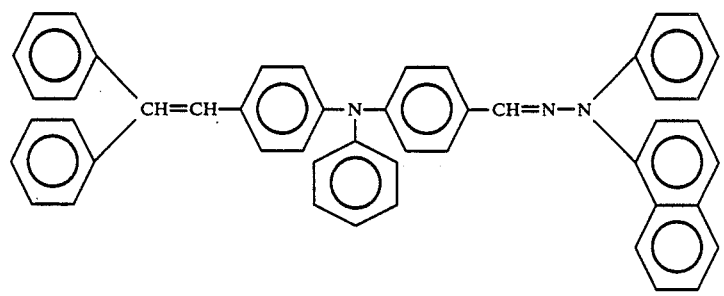
[I-23]
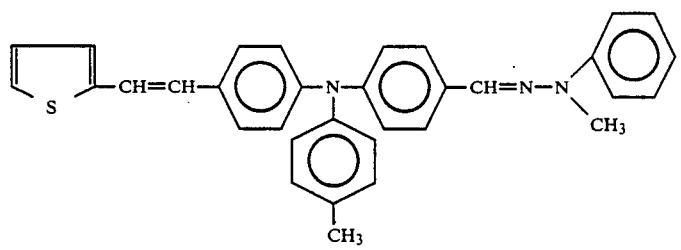
[I-24]
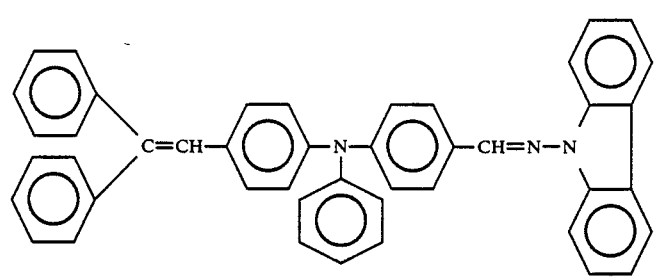
[I-25]

-continued
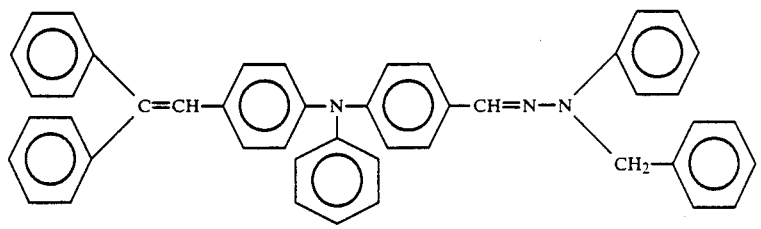
[I-26]
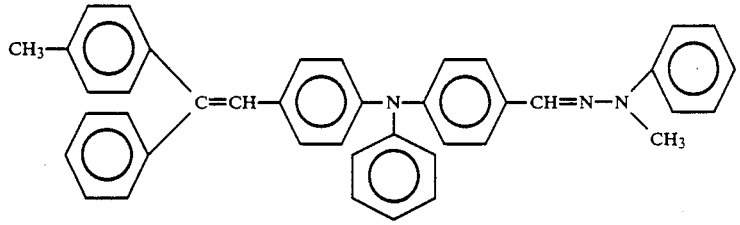
[I-27]
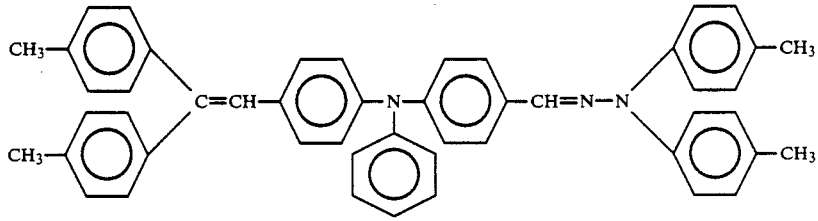
[I-28]
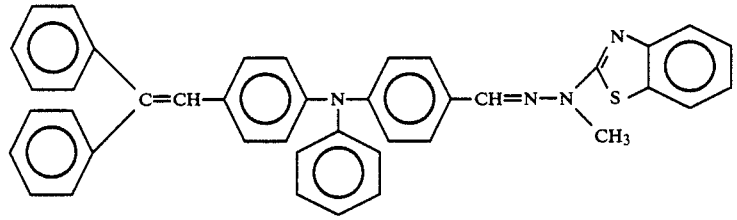
[I-29]
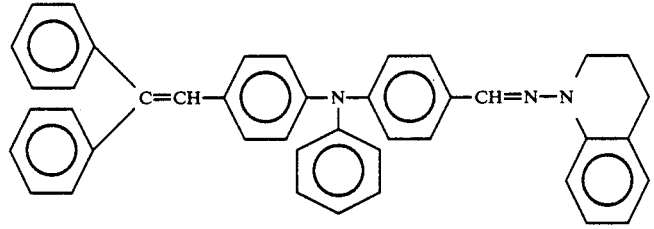
[I-30]
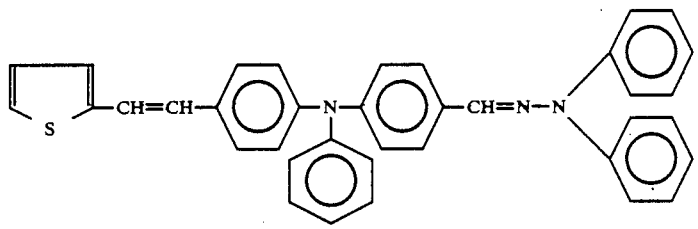
[I-31]
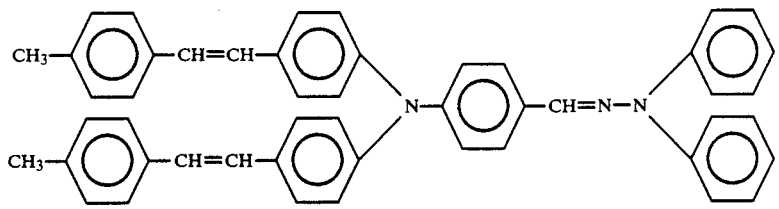
[I-32]

-continued
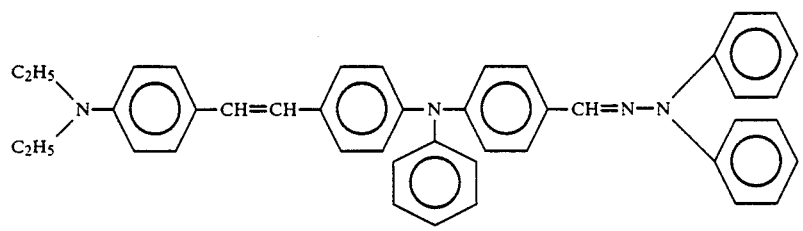
[I-33]
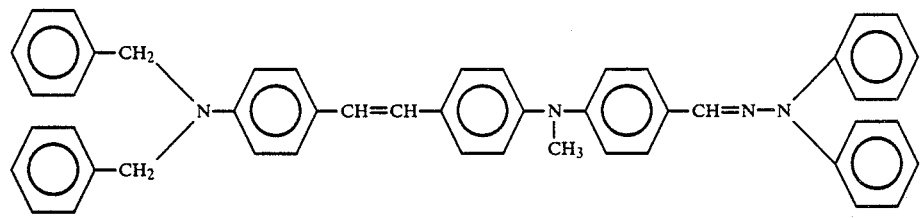
[I-34]
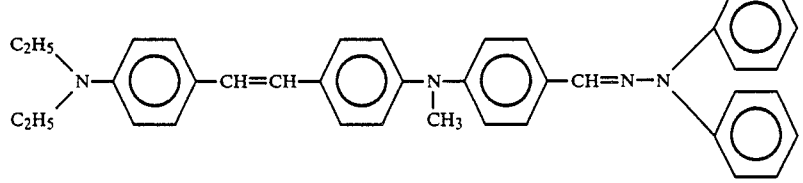
[I-35]
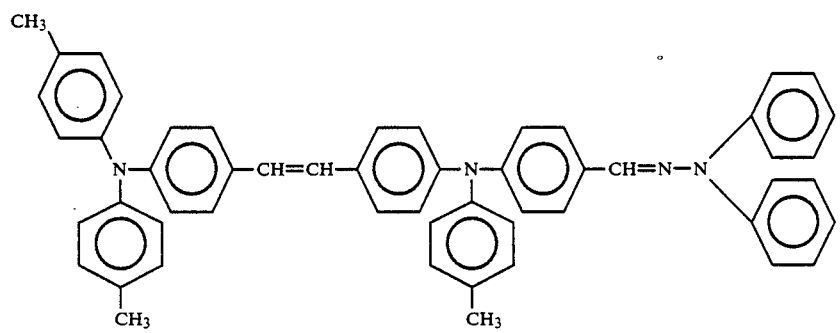
[I-36]
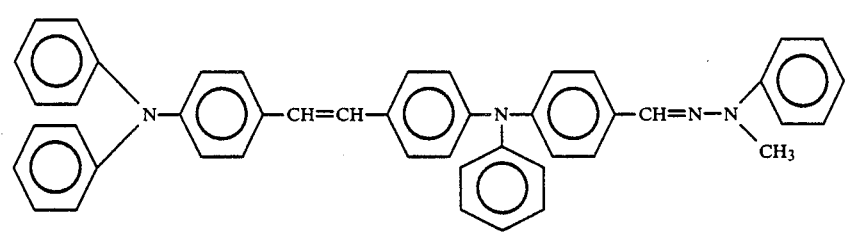
[I-37]
Preferable hydrazone compounds among those compounds as above described are (I-4), (I-7), (I-8), (I-9), (I-11), (I-14), (I-16), (I-17), (I-18), (I-19), (I-22), (I-23), (I-27), (I-28), (I-29), (I-30).
Examples of preferred hydrazone compounds of the present invention represented by the formula (III) are those having the following structual formula. These examples are in no way limitative.

[III-1]
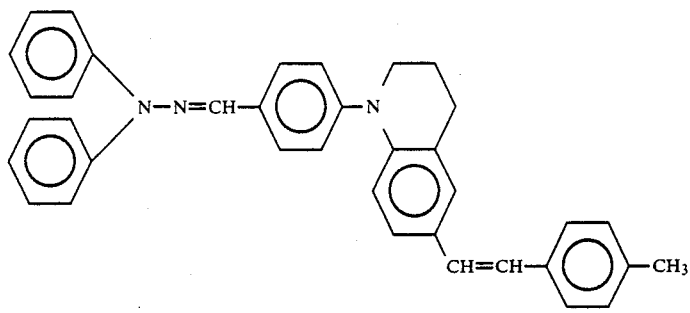
[III-2]
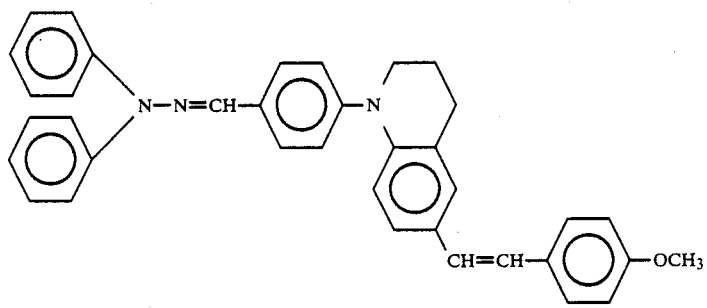
[III-3]
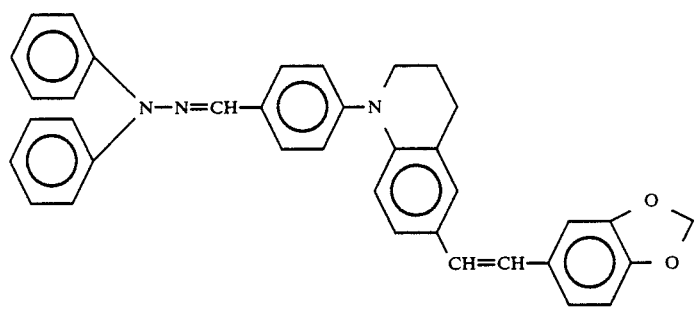
[III-4]
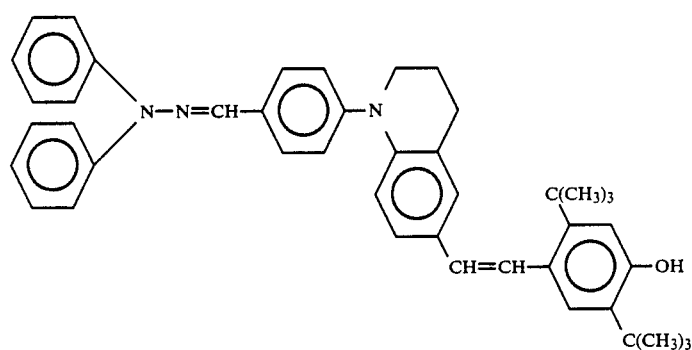

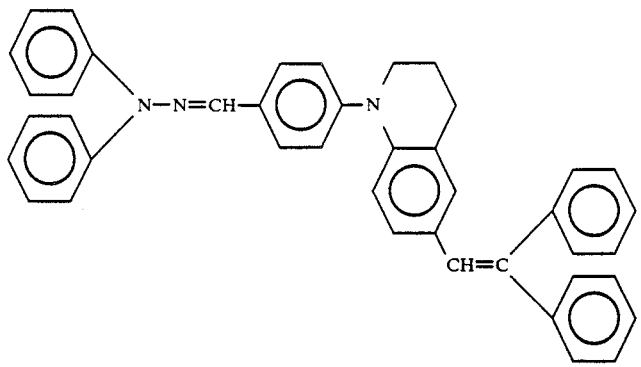
[III-5]
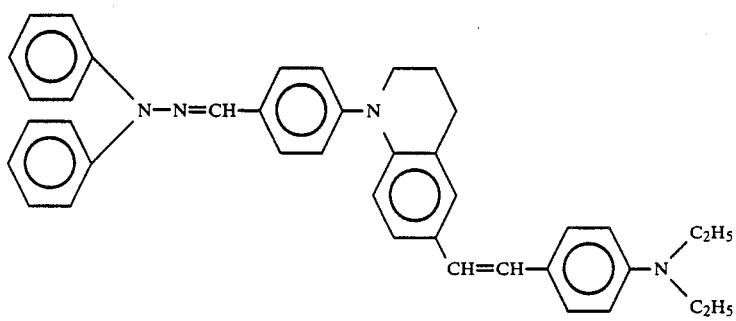
[III-6]
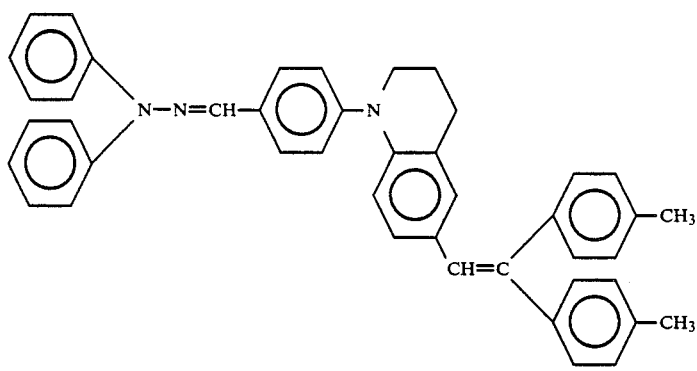
[III-7]
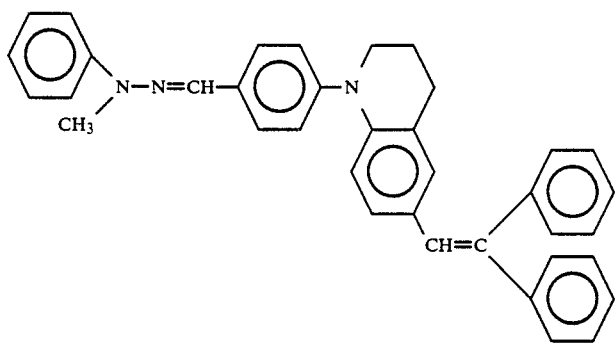
[III-8]

-continued
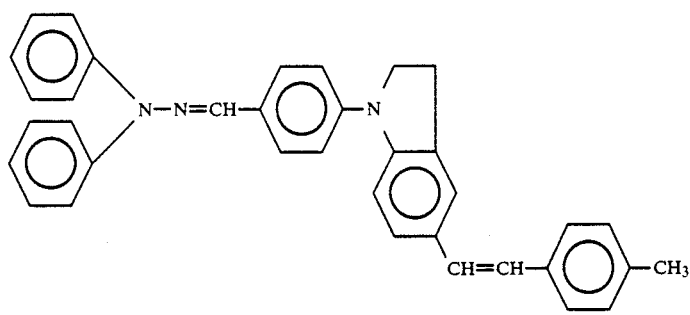
[III-9]
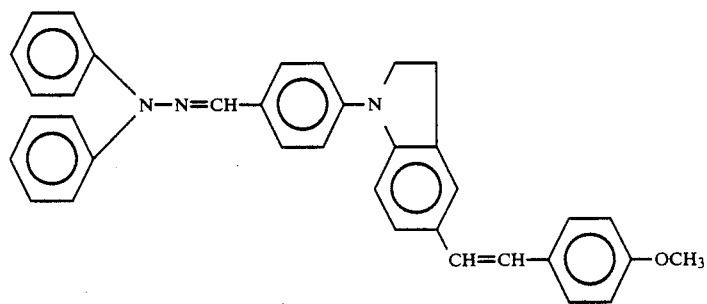
[III-10]
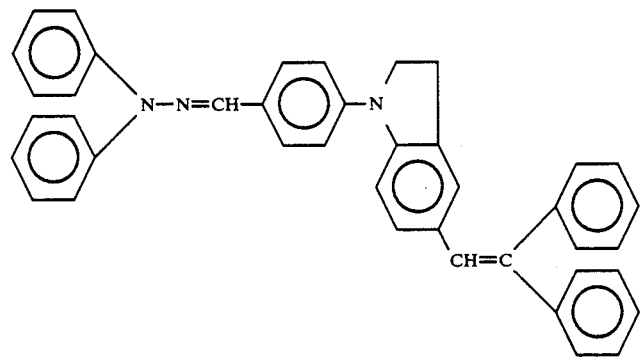
[III-11]
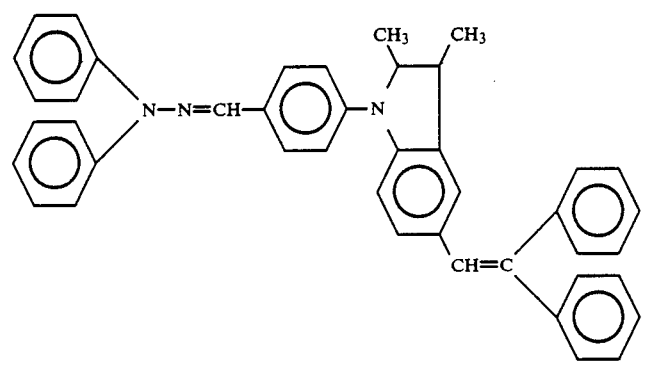
[III-12]

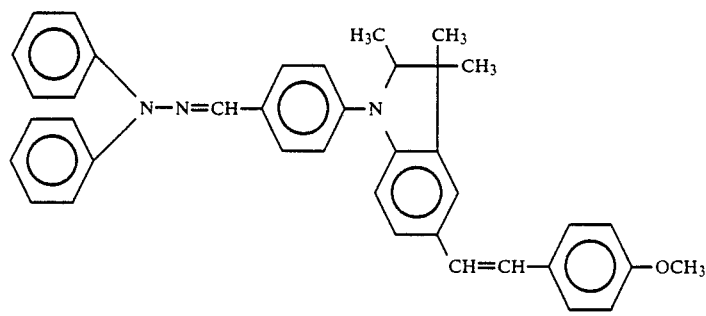
[III-13]
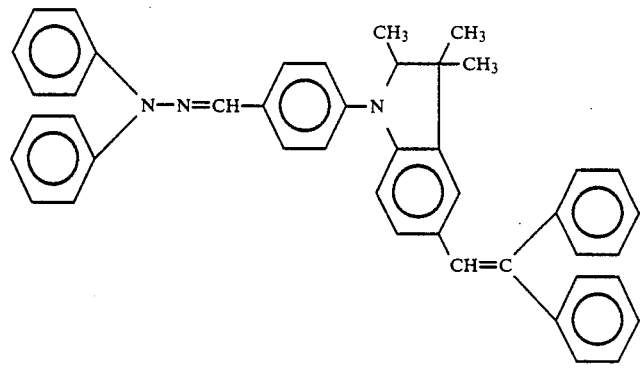
[III-14]
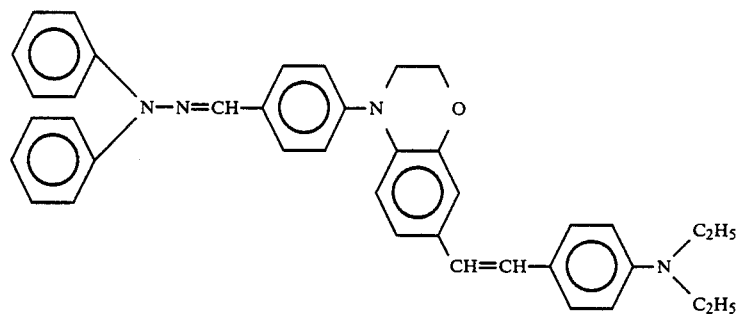
[III-15]
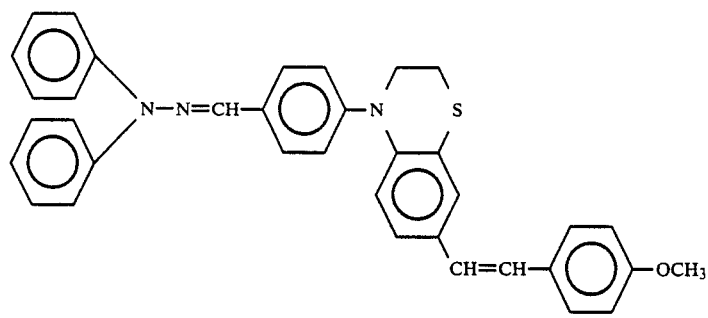
[III-16]
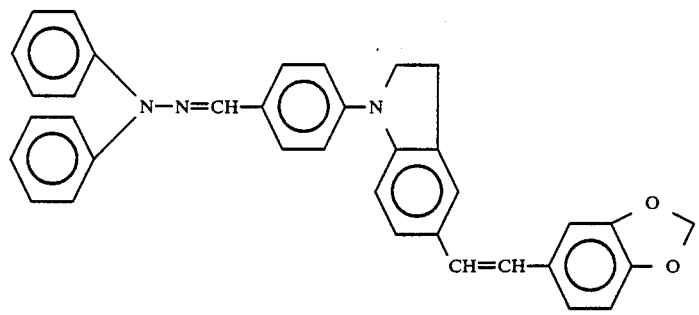
[III-17]

-continued
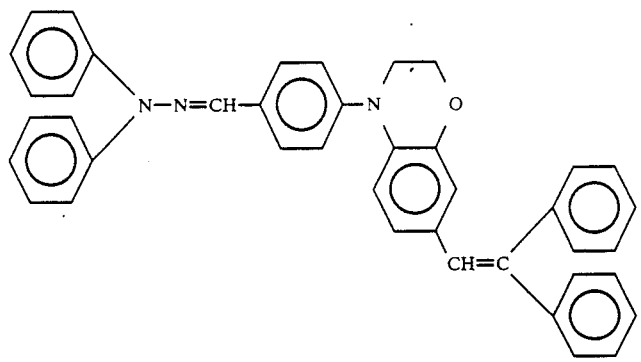
[III-18]
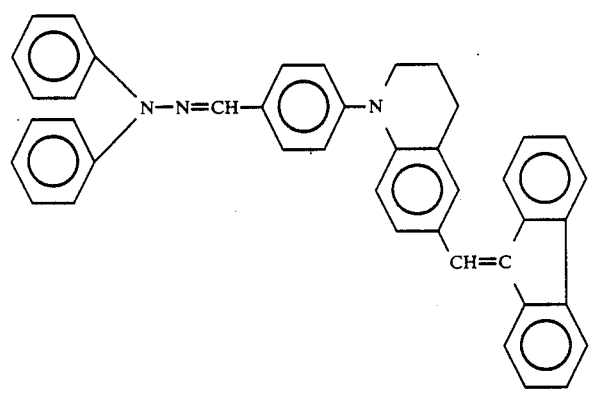
[III-19]
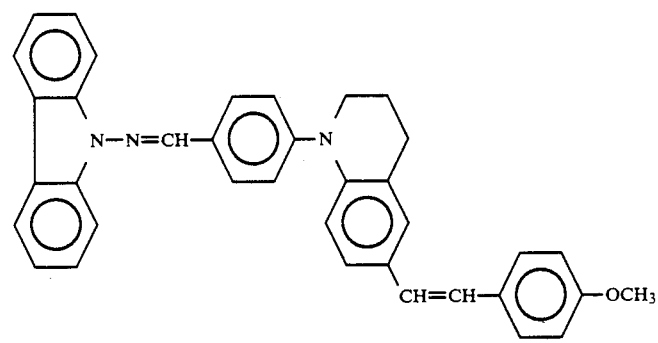
[III-20]
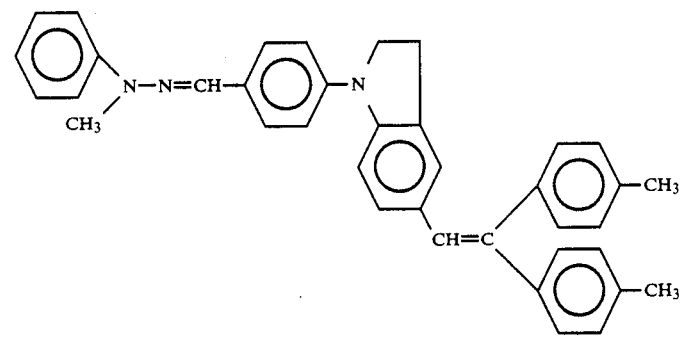
[III-21]

-continued
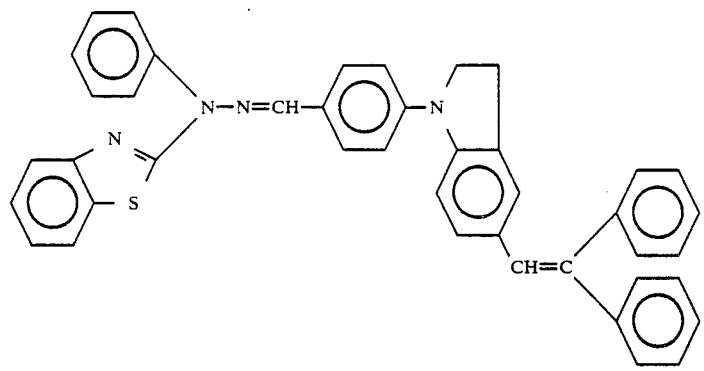
[III-22]
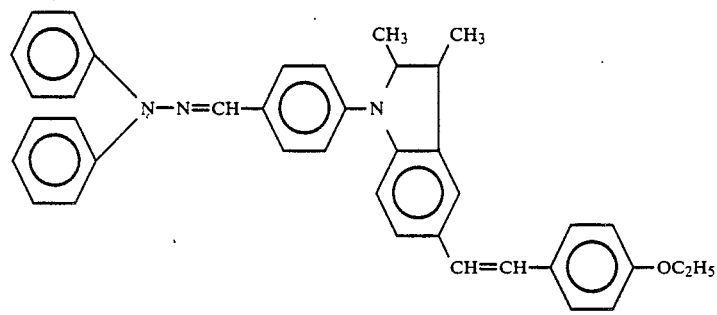
[III-23]
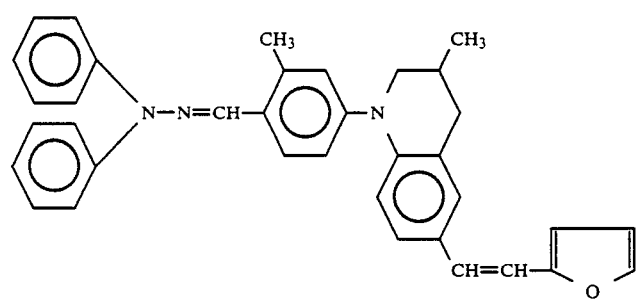
[III-24]
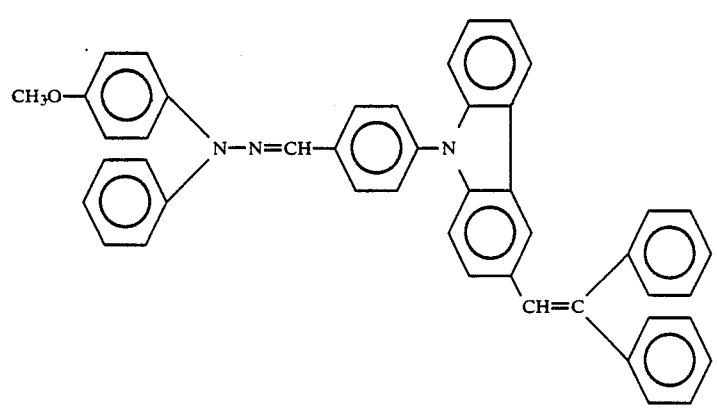
[III-25]

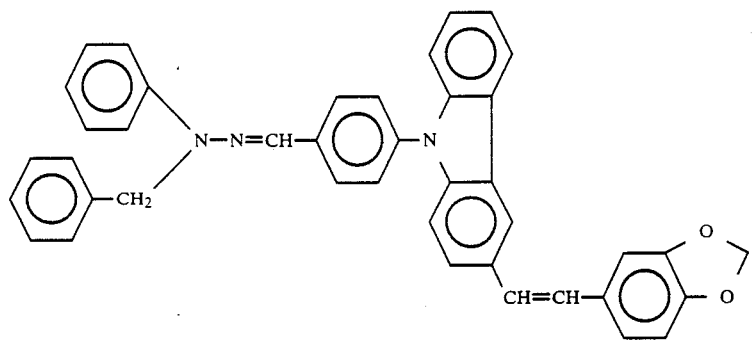
[III-26]
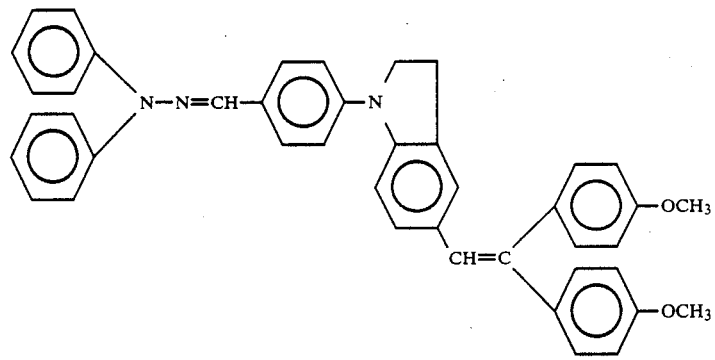
[III-27]
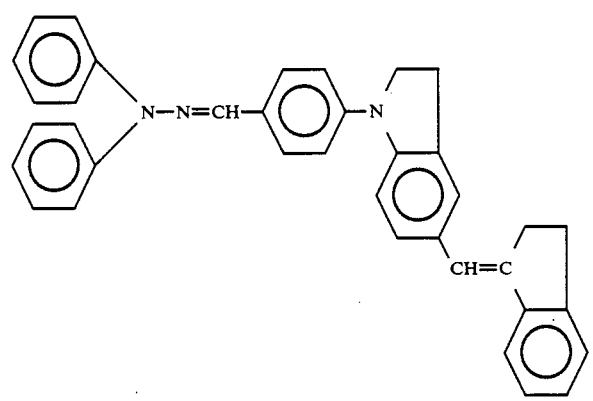
[III-28]
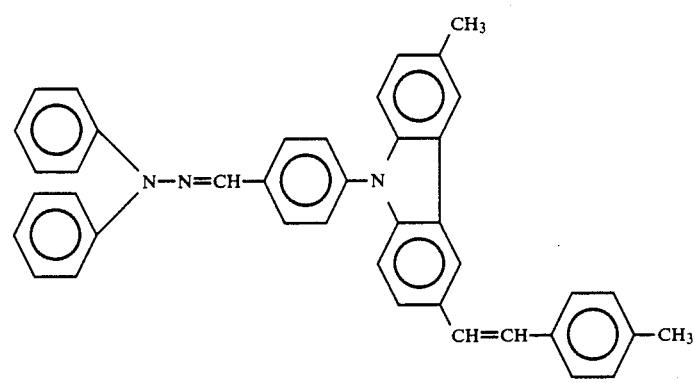
[III-29]

-continued
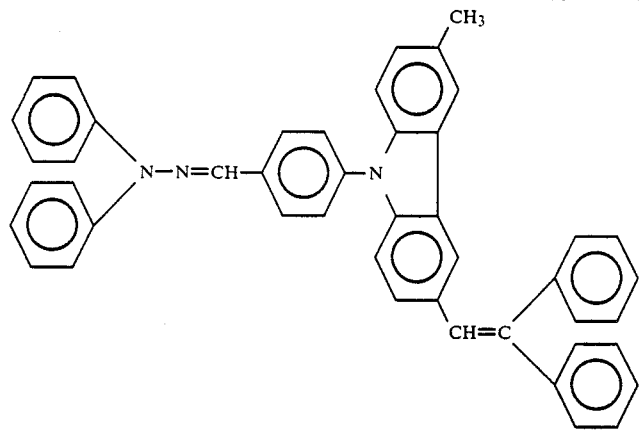
[III-30]
Preferable hydrazone compounds among those compounds as above described are (III-5), (III-6), (III-7), (III-8), (III-11), (III-12), (III-14), (III-15), (III-18), (III-21), (III-22), (III-25), (III-27), (III-30).
Examples of preferred hydrazone compounds of the present invention represented by the formula (IV) are those having the following structual formula. These examples are in no way limitative.
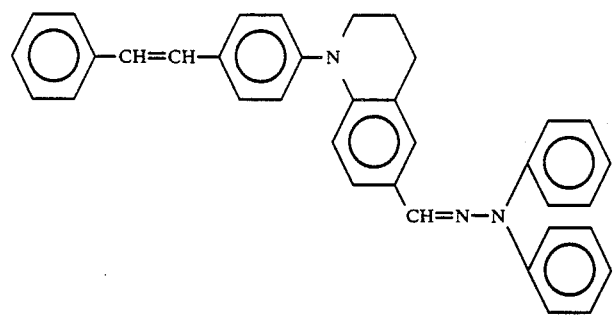
[IV-1]
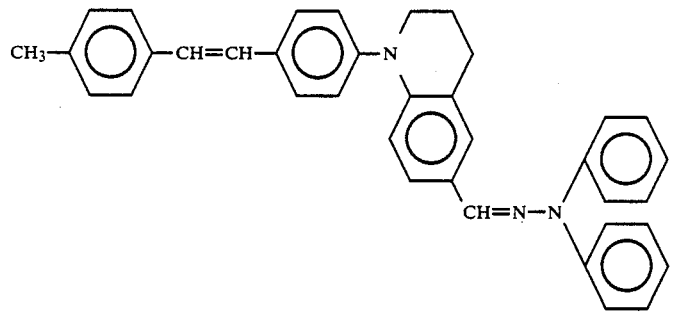
[IV-2]
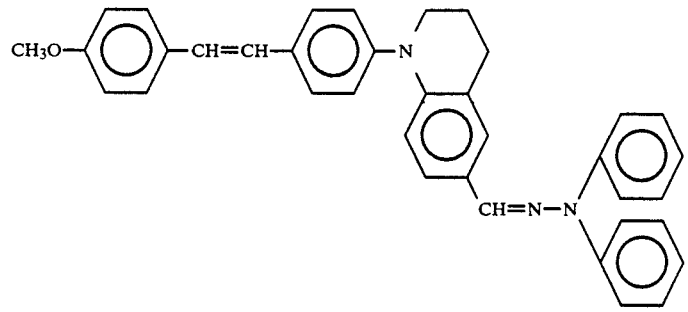
[IV-3]

-continued
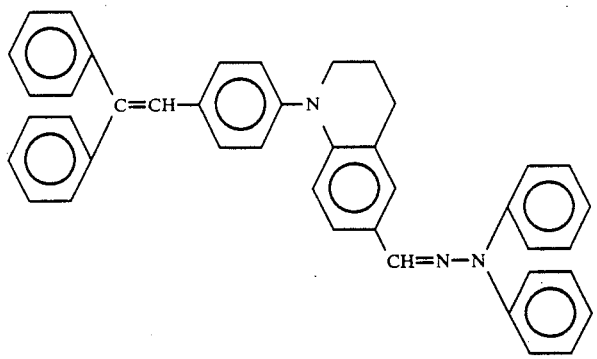
[IV-4]
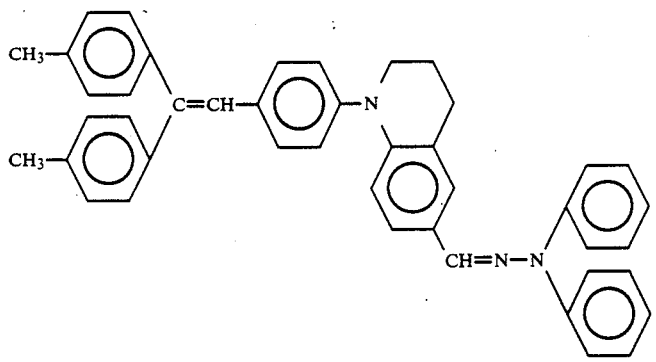
[IV-5]
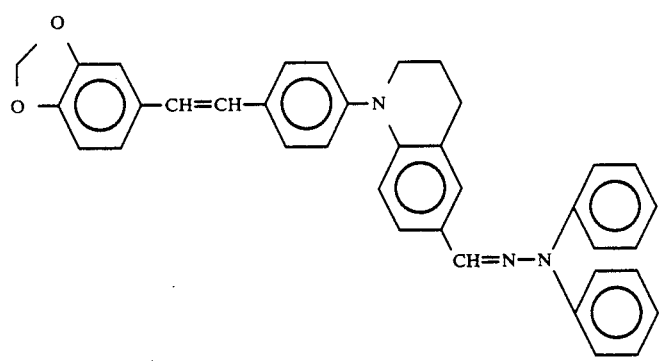
[IV-6]
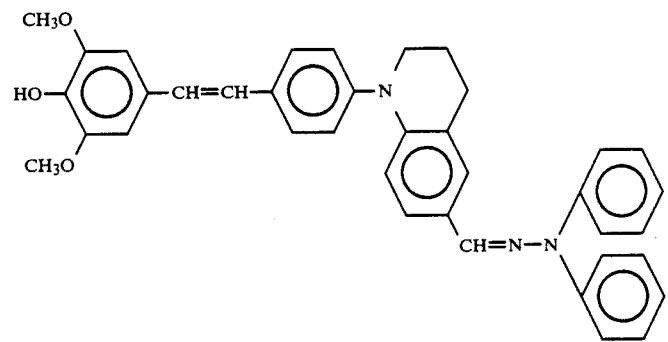
[IV-7]

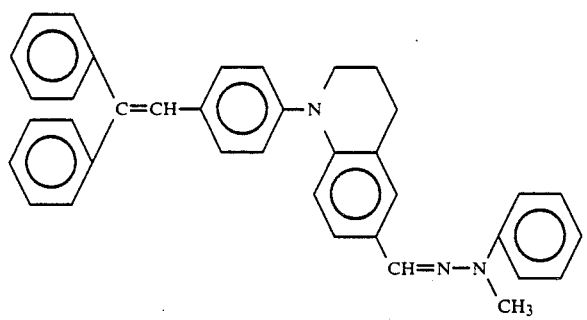
[IV-8]
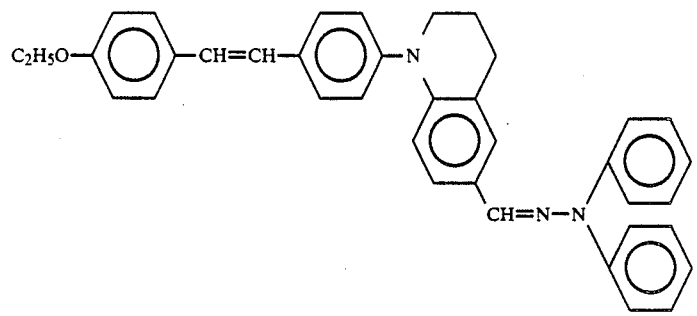
[IV-9]
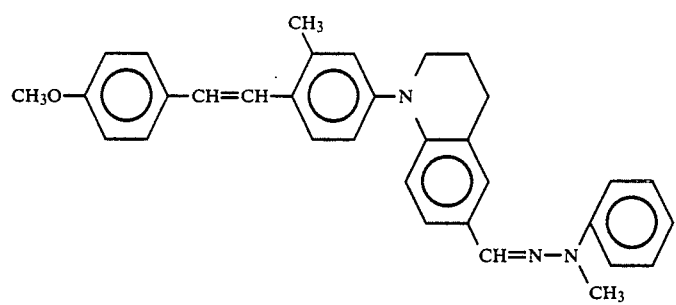
[IV-10]
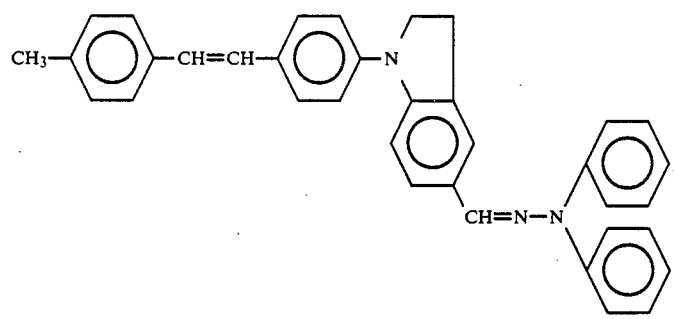
[IV-11]
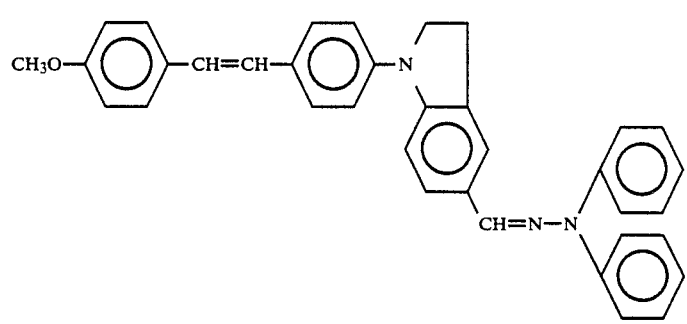
[IV-12]

[IV-13]
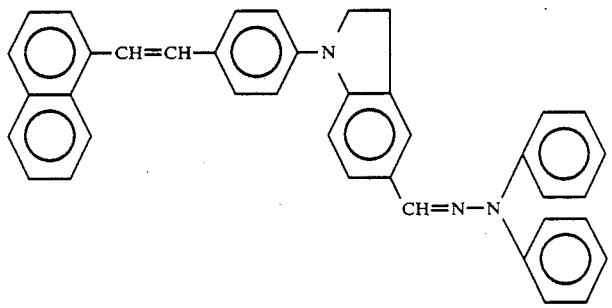
[IV-14]
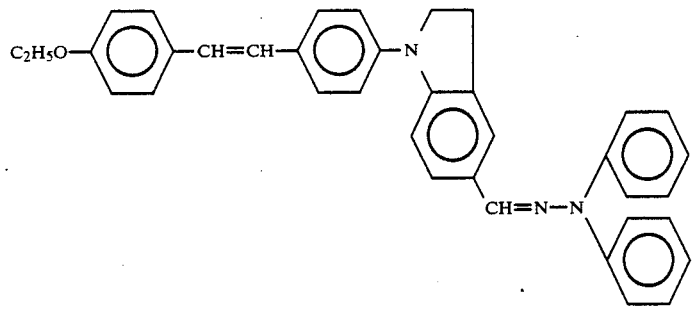
[IV-15]
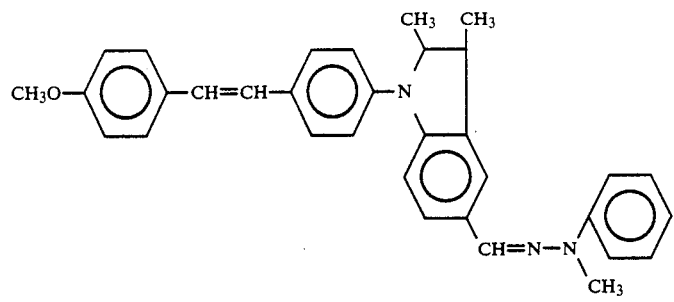
[IV-16]
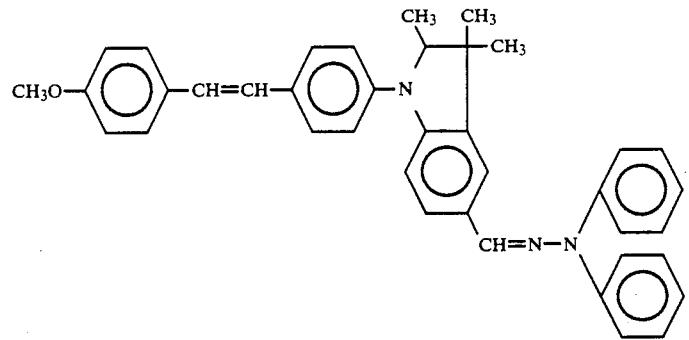
[IV-17]
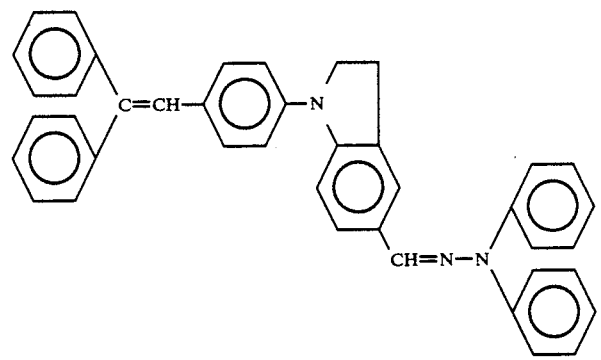

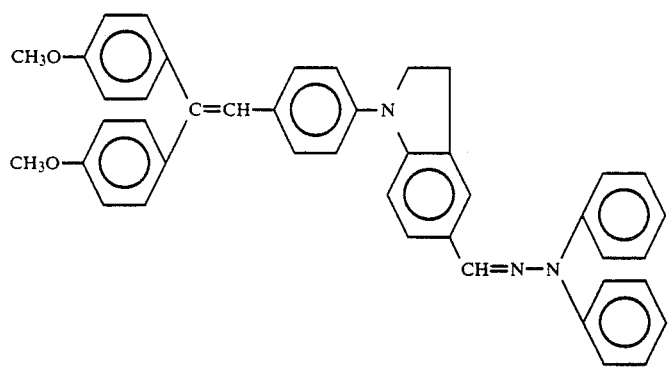
[IV-18]
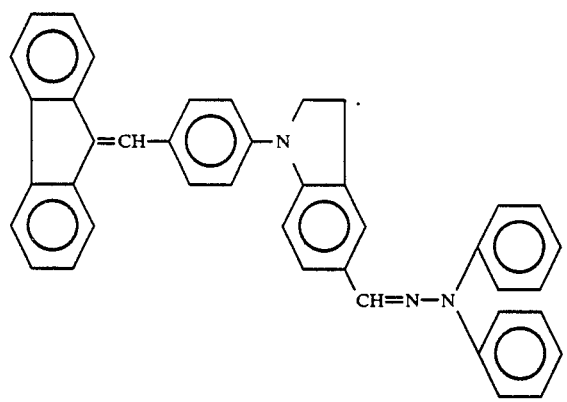
[IV-19]
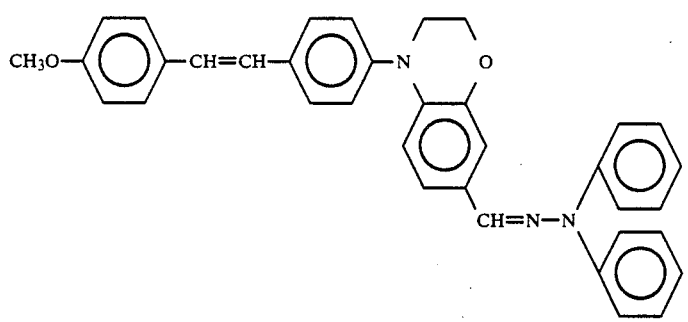
[IV-20]
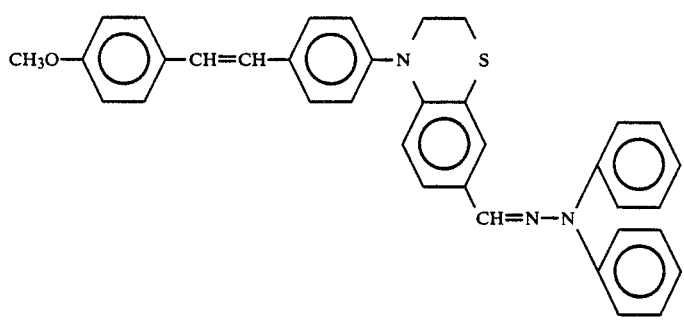
[IV-21]

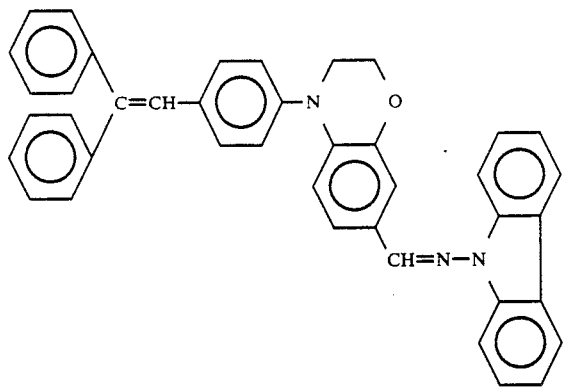
[IV-22]
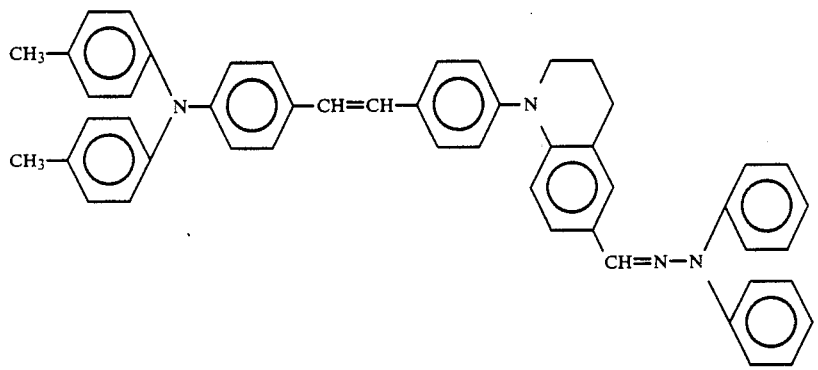
[IV-23]
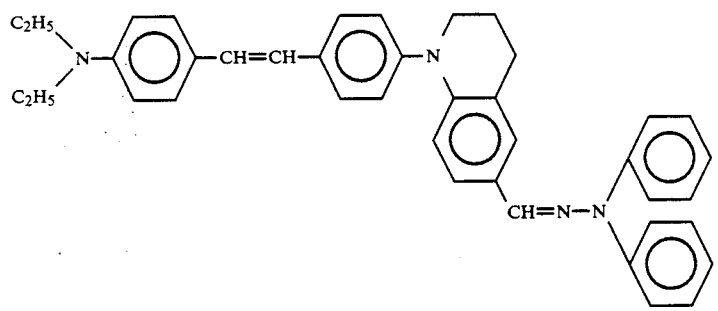
[IV-24]
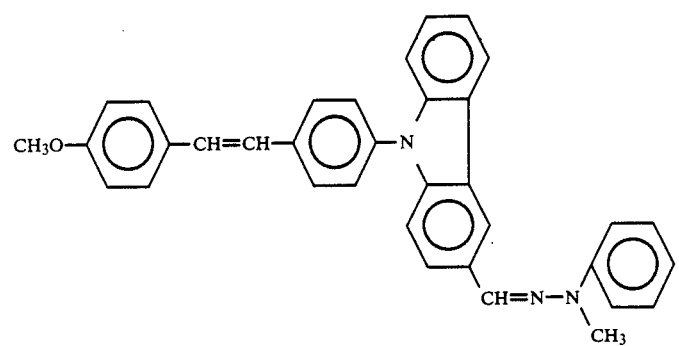
[IV-25]

[IV-26]
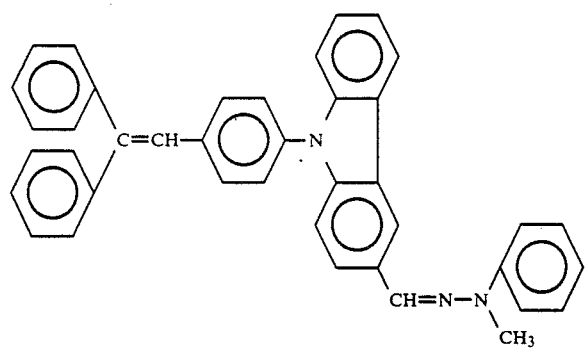
[IV-27]
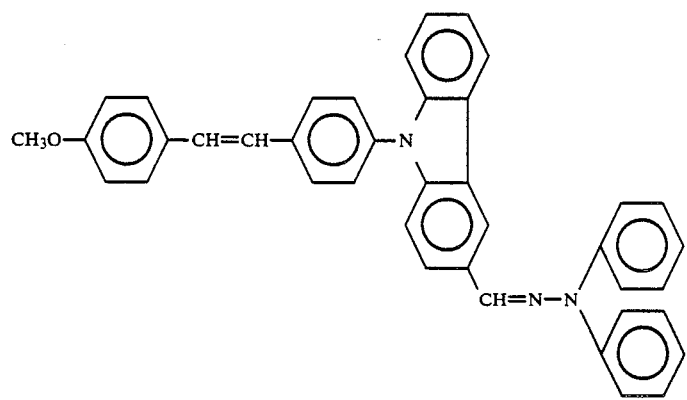
[IV-28]
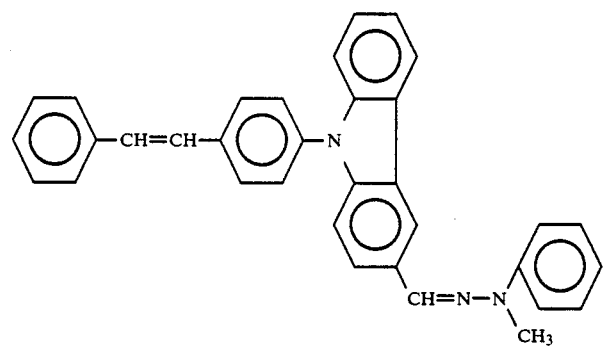
[IV-29]
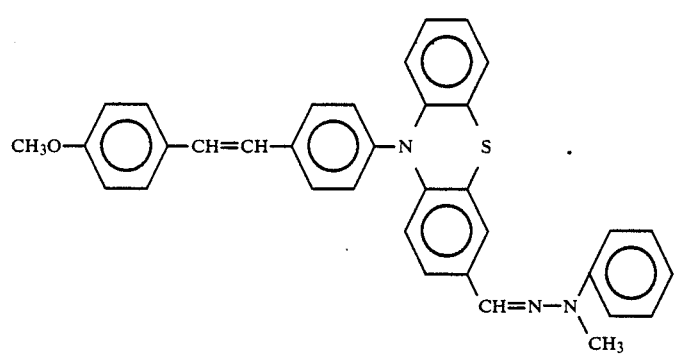

-continued

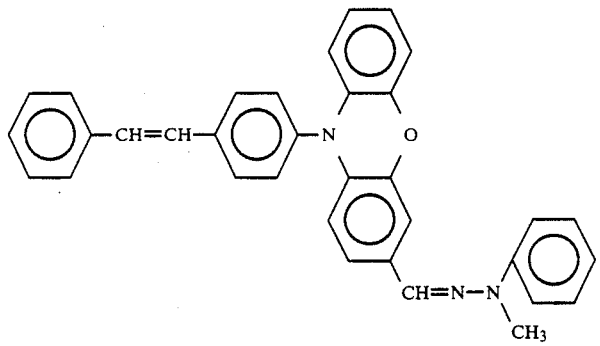

[IV-30]

Preferable hydrazone compounds among those compounds as above described are (IV-4), (IV-5), (IV-8), (IV-17), (IV-18), (IV-22), (IV-23), (IV-24), (IV-26).

A hydrazone compound represented by the general formual (I) may be synthesized by a known method.

For example, an aldehyde compound represented by the general formula (V):

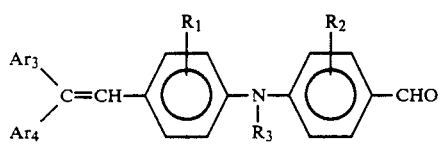

[V]

wherein $R_1R_2$, $R_3$, $Ar_3$, $Ar_4$ are same as those in the general formula (I); is condensed with a hydrazine compound represented by the general formula (VI);

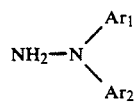

[VI]

wherein $Ar_1$, $Ar_2$ are same as those in the general formula (I).

The reaction is carried out in general by removing eliminated $H_2O$ (water) by azeotropic distillation with a solvent, for example, aromatic solvents such as benzene, toluene, xylene and the like, alcohols such as methanol, ethanol, propanol, butanol and the like, or in the presence of a catalyst such as potassium acetate, p-toluenesulfonic acid, acetic acid and the like.

A photosensitive member of the present invention has a photosensitive layer comprising one or more hydrazone compounds represented by the general formula (I).

The present invention may be applied to any type of photosensitive members per se known. For example, there is known a phtosensitive member of a mono-layer type with a charge generating material and a hydrazone compound dispersed in a binder resin on a substrate, or a so-called laminated type with a charge generating layer containing a charge generating material as a main component on a substrate, and a charge transporting layer on the charge generating layer. A hydrazone compound of the present invention is a photoconductive material and functions as a charge transporting material, which transports effectively charge carriers generated by absorbing light.

In order to form a photosensitive member of a mono-layer type, fine particles of a charge generating material are dispersed in a solution containing a hydrazone compound as a charge transporting compound and resin. The dispersion solution is coated on the electrically conductive substrate and dried. The thickness of a photosensitive layer is 3–30 μm, preferably 5–20 μm. The sensitivity is poor if a hydrazone compound as a charge transporting material and a charge generating material are used in an insufficient quantity, whereas the chargeability becomes poor and the mechanical strength of photosensitive layer is inadequate if used to excess. Therefore, the amount of an hydrazone compound contained in the photosensitive layer is within the range of 0.2–30 parts by weight, preferably, 0.2–20 parts by weight on the basis of one part by weight of resin. The amount of a charge generating compound is contained at the content of 0.01–3 parts by weight, preferably 0.2–2 parts by weight on the basis of one part by weight of resin.

In order to form a photosensitive member of a laminated type, a charge generating material is deposited in a vacuum on an electrically conductive substrate, a charge generating material is dissolved in a solvent such as amine to apply onto an electrically conductive substrate or an application solution containing a charge generating material and, if necessary, binder resin dissolved in an appropriate solvent is applied onto an electrically conductive substrate to be dried, for the formation of a charge generating layer on the electrically conductive substrate. Then, a solution containing a charge transporting material and a binder is applied onto the charge generating layer followed by drying for the formation of a charge transporting layer. The thickness of a charge generating layer is 4 μm or less, preferably, 2 μm or less. It is suitable that the charge-transporting layer has a thickness in the range 3–30 μm, preferably 5–20 μm.

The content of charge transporting materials in the charge-transporting layer is 0.2–2 parts by weight, preferably 0.3–1.3 parts by weight on the basis of one part by weight of the binder resin.

A photosensitive member of the present invention permits, in combination with a binder resin, the use of a plasticizer, such as halogenated paraffin, polybiphenyl chloride, dimethyl naphthalene, dibutyl phthalate or o-terphenyl, the use of an electron-attractive sensitizer, such as chloranyl, tetracyanoethylene, 2,4,7-trinitrofluorenone, 5,6-dicyanobenzoquinone, tetracyanoquinodimethane, tetrachlorophthalic anhydride, or 3,5-dinitrobenzoic acid, and the use of a sensitizer, such as methyl violet, rhodamine B, cyanine dye, pyrylium salt, and thiapyrylium salt.

An anti-oxidizing agent, an ultraviolet light absorber, a dispersing agent, an anti settling agent and the like may be contained in a photosensitive member.

Some examples of suitable binders for the production of a photosensitive member are thermoplastic resins such as saturated polyester, polyamide, acrylic, ethylene-vinyl acetate copolymer, ion cross-linked olefin copolymer (ionomer), styrene-butadiene block copolymer, polycarbonate, vinyl chloride-vinyl acetate copolymer, cellulose ester, polyimide, styrol, etc., and thermosetting resins such as, epoxy, urethane, silicone, phenolic, melamine, xylene, alkyd, thermosetting acrylic, etc., and photocuring resins, and photoconductive resins such as poly-N-vinyl carbazole, polyvinyl pyrene, polyvinyl anthracene, polyvinyl pyrrole, etc., all named without any significance of restricting the use to them. Any of these resins can be used singly or in combination with other resins. It is desirable for any of these electrically insulative resins to have a volume resistance of $1 \times 10^{12}$ Ω·cm or more when measured singly.

Examples of charge generating materials are organic substances such as bisazo pigments, triarylmethane dyes, thiazine dyes, oxazine dyes, xanthene dyes, cyanine coloring agents, styryl coloring agents, pyrylium dyes, azo pigments, quinacridone pigments, indigo pigments, perylene pigments, polycyclic quinone pigments, bisbenzimidazole pigments, indanthrone pigments, squalylium pigments, azulene dye stuff, phthalocyanine pigments and the like, and inorganic substances such as selenium, selenium-tellurium, selenium arsenic, cadmium sulfide, amorphous silicon and the like. Any other material is also usable insofar as it generates charge carriers very efficiently upon absorption of light.

An electrically conductive substrate is exemplified by a sheet or a drum made of metal or alloy such as copper, aluminium, silver, iron, and nickel; a substrate such as a plastic film on which the foregoing metal or alloy is adhered by a vacuum-deposition method or an electroless plating method and the like; a substrate such as a plastic film and paper on which an electro- conductive layer is formed by applying or depositing electroconductive polymer, indium oxide, tin oxide etc..

FIG. 1 to FIG. 5 schematically show examples of electrophotographic photosensitive members prepared with use of hydrazone compound of the invention.

FIG. 1 shows a photosensitive member comprising a photoconductive layer 4 formed on a substrate 1 and prepared from a charge generating material 3 and a charge transporting material 2 as admixed with a binder. A hydrazone compound of the invention is used as the charge transporting material.

Figure 2:
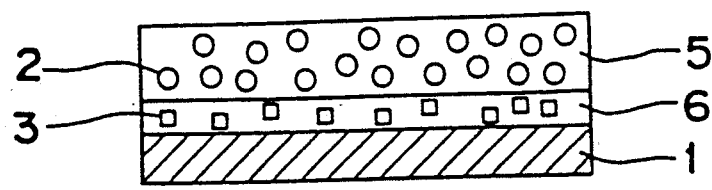
FIG. 2 is a diagram showing the structure of a photosensitive member of the function-divided type comprising a charge generating layer and a charge transporting layer which are formed on an electrically conductive substrate.

FIG. 2 shows a photosensitive member of the function-divided type comprising a charge generating layer 6 and a charge transporting layer 5 which are combined to serve as a photoconductive layer. The charge transporting layer 5 is formed on the surface of the charge generating layer 6. A hydrazone compound of the invention is incorporated in the charge transporting layer 5.

Figure 3:
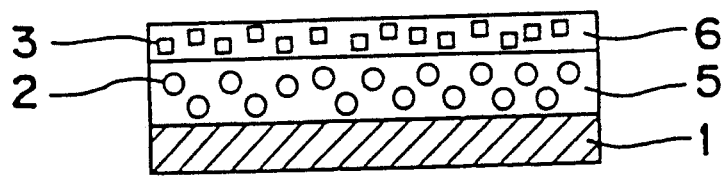
FIG. 3 is a diagram showing the structure of a member of another photosensitive member of the function-divided type comprising a charge generating layer and a charge transporting layer which are formed on an electrically conductive substrate.

FIG. 3 shows another photosensitive member of the function-divided type which, like the one shown in FIG. 2, comprises a charge generating layer 6 and a charge transporting layer 5. In converse relation to the member shown in FIG. 2, the charge generating layer 6 is formed on the surface of the charge transporting layer 5.

Figure 4:
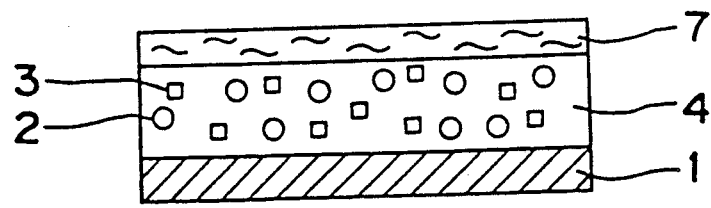
FIG. 4 is a diagram showing the structure of another dispersion-type photosensitive member comprising a photosensitive layer and a surface protective layer formed on an electrically conductive substrate.

The member shown in FIG. 4 comprises the one shown in FIG. 1 and a surface protective layer 7 formed on the surface of the photoconductive layer 4. The photoconductive layer 4 may be separated into a charge generating layer 6 and a charge transporting layer 5 to provide a photosensitive member of the function-divided type.

It is suitable that a surface protective layer is formed with polymer itself such as acrylic resin, polyaryl resin, polycarbonate resin, urethane resin, or formed by dispersing materials with low electrical resistance such as tin oxide or indium oxide.

Figure 5:
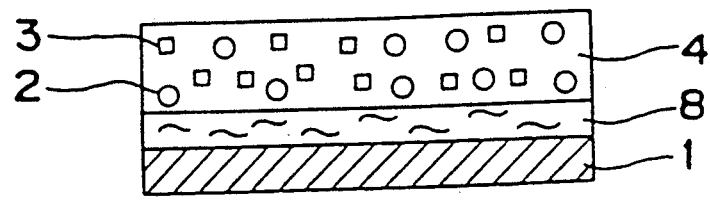
FIG. 5 is a diagram showing the structure of another dispersion-type photosensitive member comprising a photosensitive layer and an intermediate layer formed on an electrically conductive substrate.

FIG. 5 shows a photosensitive member having the same constitution as the one shown in FIG. 1 except that an intermediate layer 8 is interposed between the substrate 1 and the photoconductive layer 4. The intermediate layer 8 serves to give enhanced adhesion, afford improved coatability, protect the substrate and assure injection of charges from the substrate into the photoconductive layer with improved effectiveness.

An intermediate layer is formed with polymer itself such as polyimide, polyamide, nitrocellulose, polyvinylbutyral, polyvinylalcohol, or formed by dispersing materials with low electrical resistance such as tin oxide or indium oxide, or by depositing aluminium oxide, zinc oxide, silicon oxide and so on.

The desirable thickness of an intermediate layer is 1 μm or less.

Synthesis example (hydrazone compound(I-12))

The aldehyde compound represented by the formula below;

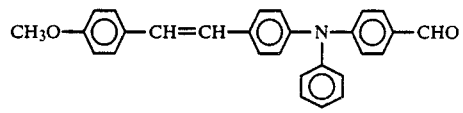

of 4.05 parts by weight was reacted with the hydrochloride of 1,1-diphenylhydrazine of 2.21 parts by weight in the presence of a small amount of acetic acid in ethanol of 200 ml at a refluxing temperature for 2 hours.

After cooling, water was added to the reaction mixture to deposit crystalline materials. The crystalline products were filtered, washed with n-hexane and recrystallized in acetonitrile for purification. Pale yellow crystalline products of 4.6 parts by weight were obtained (Yield:81%). The elemental analysis is as below;

| element | elemental analysis | | |
|---|---|---|---|
| | C | H | N |
| calcd. (%) | 84.06 | 5.78 | 7.36 |
| found (%) | 84.10 | 5.71 | 7.28 |

Synthesis example (hydrazone compound(III-5))

The aldehyde compound represented by the formula below;

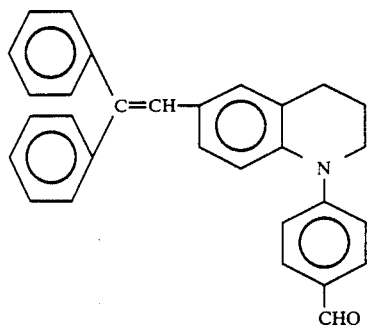

of 4.15 parts by weight was reacted with the hydrochloride of 1,1-diphenylhydrazine of 2.21 parts by weight in the presence of a small amount of acetic acid in ethanol of 200 ml at a refluxing temperature for 2 hours.

After cooling, water was added to the reaction mixture to deposit crystalline materials. The crystalline products were filtered, washed with n-hexane and recrystallized in acetone-methanol for purification. Yellow crystalline products of 3.4 parts by weight were obtained (Yield:77.8%). The elemental analysis is as below;

| element | elemental analysis | | |
|---|---|---|---|
| | C | H | N |
| calcd. (%) | 82.38 | 8.01 | 9.61 |
| found (%) | 82.49 | 7.95 | 9.66 |

Synthesis example (hydrazone compound(IV-4))

The aldehyde compound represented by the formula below;

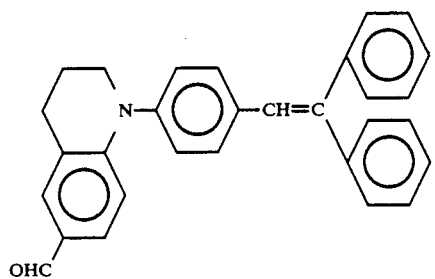

of 4.15 parts by weight was reacted with the hydrochloride of 1,1-diphenylhydrazine of 2.21 parts by weight in the presence of a small amount of acetic acid in ethanol of 200 ml at a refluxing temperature for 2 hours.

After cooling, water was added to the reaction mixture to deposit crystalline materials. The crystalline products were filtered, washed with n-hexane and recrystallized in acetone-methanol for purification. Yellow crystalline products of 3.5 parts by weight were obtained (Yield:80.1%). The elemental analysis is as below;

| element | elemental analysis | | |
|---|---|---|---|
| | C | H | N |
| calcd. (%) | 82.38 | 8.01 | 9.61 |
| found (%) | 82.54 | 7.96 | 9.65 |

"Part" means "part by weight" in following Examples so long as it is particularly specified.

EXAMPLE 1

The bisazo compound represented by the following formula (A);

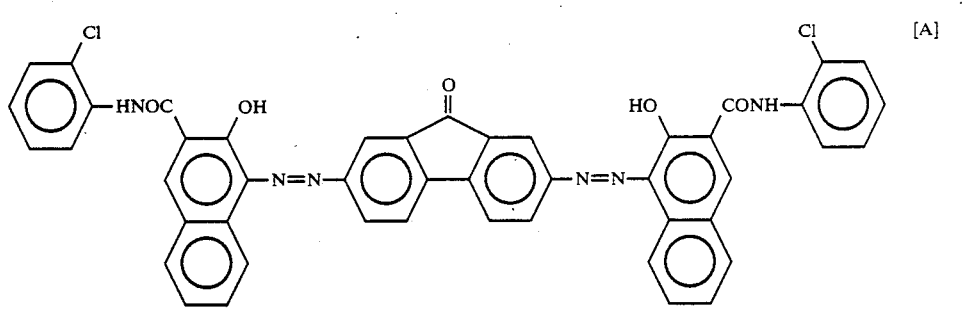

of 0.45 parts by weight and 0.45 parts by weight of polyester resin (Vylon 200 made by Toyobo K.K.) and 50 parts by weight of cyclohexanone were taken in Sand grinder for dispersion. The dispersion solution of the bisazo pigment was applied onto aluminotype-Mylar of 100 μm in thickness by a film applicator to form a charge generating layer so that a thickness of the layer might be 0.3 g/m² after dried. A solution of 70 parts of the hydrazone compound (I-4), and 70 parts of polycarbonate resin (K-1300; made by Teijin Kasei K.K.) dissolved in 400 parts of 1,4-dioxane was applied onto the above formed charge generating layer to form a charge transporting layer so that the thickness of the layer might be 16 μm after drid. Thus, a photosensitive member with the two layers was prepared.

The resultant photosensitive member was incorporated into a commercial electrophotographic copying machine (EP-470Z, made by Minolta Camera K.K.) and tested with application of a voltage of $-6$ Kv to the d.c. power-supply to measure the initial surface potential Vo (V), the amount of exposure required for Vo to reduce to half of Vo (E½ (lux·sec)), and the potential decay rate $DDR_1$ (%) when the member was allowed to stand in the dark for 1 second after charging.

The results are shown in Table 1.

EXAMPLES 2–4

Photosensitive members with the same structure as that of Example 1 were prepared in a manner similar to Exmple 1 except that the hydrazone compounds(I-5), (I-8), (I-9) were used respectively instead of the hydrazone compound(I-4).

$V_0$, E½, $DDR_1$ were measured on the resultant photosensitive members in a manner similar to the example 1.

The results are shown in Table 1.

EXAMPLE 5

The bisazo compound represented by the following formula (B);

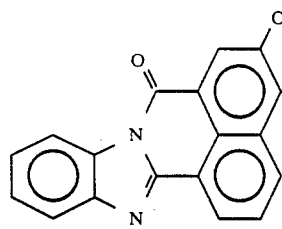 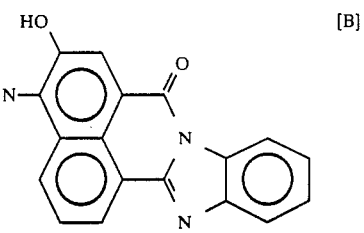

of 0.45 parts by weight and 0.45 parts by weight of polystyrene (molecular weight;40000) and 50 parts by weight of cyclohexanone were taken in Sand grinder for dispersion. The dispersion solution of he bisazo compound was applied onto aluminotype-Mylar of 100 μm in thickness by a film applicator to form a charge generating layer so that a thickness of the layer might be 0.3 g/m² after dried. A solution of 70 parts of the hydrazone compound (I-10), and 70 parts of polyarylate resin (U-100;made by Yunitsika K.K.) dissolved in 400 parts of 1,4-dioxane was applied onto the above formed charge generating layer to form a charge transporting layer so that the thickness of the layer might be 16 μm after drid. Thus, a photosensitive member with the two layers was prepared.

$V_0$, $E_{\frac{1}{2}}$, $DDR_1$ were measured on the resultant photosensitive member in a manner similar to the example 1.

The results are shown in Table 1.

EXAMPLES 6-8

Photosensitive members with the same structure as that of Example 5 were prepared in a manner similar to Example 5 except that the hydrazone compounds(I-11), (I-12), (I-13) were used respectively instead of the hydrazone compound (I-10).

$V_0$, $E_{\frac{1}{2}}$, $DDR_1$ were measured on the resultant photosensitive members in a manner similar to the example 1.

The results are shown in Table 1.

EXAMPLE 9

Copper-phthalocyanine of 50 parts and tetranitro-copper-phthalocyanine of 0.2 parts were dissolved in conc.sulfuric acid (98%) of 500 parts while stirring. The obtained solution was poured into water of 5000 parts to deposit a photoconductive composition of copper-phthalocyanine and tetranitro-copper-phthalocyanine. The deposited composition was filtered, washed with water and dried in vacuum at 120° C.

The obtained composition of 10 parts, a thermosetting acrylic resin (Acrydick A405; made by Dainippon Ink K.K. of 22.5), a melamine resin (Super Beckamine J820; made by Dainippon Ink K.K.) of 7.5 parts, a hydrazone compound (I-14) of 15 parts, a mixed solvent (methyl ethyl ketone:xylene=1:1) of 100 parts were taken into a ball mill for dispersion for 48 hours to obtain a photosensitive coating solution. The coating solution was applied onto an aluminium substrate to form a photosensitive layer of about 15 μm in thickness after dried.

The resultant photosensitive member was tested with the application of a voltage of +6 KV to the d.c. power to measure $V_0$, $E_{\frac{1}{2}}$, $DDR_1$.

The results are shown in Table 1.

EXAMPLES 10-12

Photosensitive members with the same structure as that of Example 9 were prepared in a manner similar to Example 9 except that the hydrazone compounds(I-15), (I-16), (I-17) were used respectively instead of the hydrazone compound(I-14).

$V_0$, $E_{\frac{1}{2}}$, $DDR_1$ were measured on the resultant photosensitive members in a manner similar to the example 9.

The results are shown in Table 1.

EXAMPLES 13-16

Photosensitive members with the same structure as that of Example 1 were prepared in a manner similar to Example 1 except that the hydrazone compounds(III-2), (III-3), (III-5), (III-6) were used respectively instead of the hydrazone compound(I-4).

$V_0$, $E_{\frac{1}{2}}$, $DDR_1$ were measured on the resultant photosensitive members in a manner similar to the example 1.

The results are shown in Table 1.

EXAMPLE 17

The bisazo compound represented by the following formula (C);

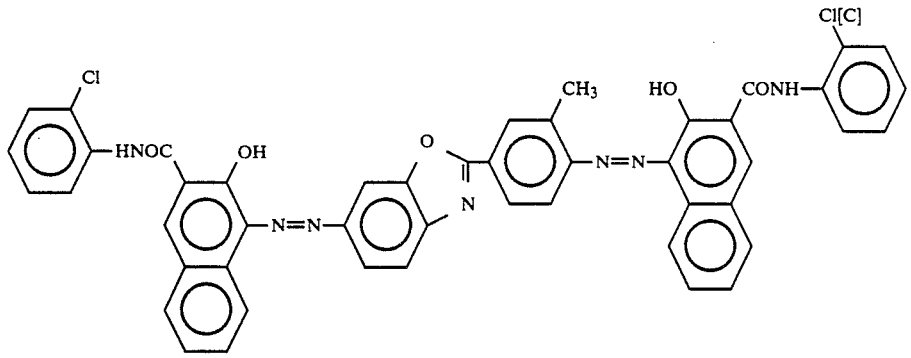

of 0.45 parts by weight and 0.45 parts by weight of polystyrene (molecular weight;40000) and 50 parts by weight of cyclohexanone were taken in Sand grinder for dispersion. The dispersion solution of he bisazo compound was applied onto aluminotype-Mylar of 100 μm in thickness by a film applicator to form a charge generating layer so that a thickness of the layer might be 0.3 g/m² after dried. A solution of 70 parts of the hydrazone compound (III-7), and 70 parts of polyarylate resin (U-100;made by Yunitsika K.K.) dissolved in 400 parts of 1,4-dioxane was applied onto the above formed charge generating layer to form a charge transporting layer so that the thickness of the layer might be 16 μm after drid. Thus, a photosensitive member with the two layers was prepared.

$V_0$, $E_{\frac{1}{2}}$, $DDR_1$ were measured on the resultant photosensitive member in a manner similar to the example 1.

The results are shown in Table 1.

EXAMPLES 18–20

Photosensitive members with the same structure as that of Example 17 were prepared in a manner similar to Example 17 except that the hydrazone compounds(III-10), (III-11), (III-15) were used respectively instead of the hydrazone compound (III-7).

$V_0$, $E_{\frac{1}{2}}$, $DDR_1$ were measured on the resultant photosensitive members in a manner similar to the example 1.

The results are shown in Table 1.

EXAMPLES 21–24

Photosensitive members with the same structure as that of Example 9 were prepared in a manner similar to Example 9 except that the hydrazone compounds(III-17), (III-21), (III-25), (III-27) were used respectively instead of the hydrazone compound (I-14).

$V_0$, $E_{\frac{1}{2}}$, $DDR_1$ were measured on the resultant photosensitive members in a manner similar to the example 1.

The results are shown in Table 1.

EXAMPLES 25–28

Photosensitive members with the same structure as that of Example 1 were prepared in a manner similar to Example 1 except that the hydrazone compounds(IV-4), (IV-5), (IV-6), (IV-8) were used respectively instead of the hydrazone compound (I-4).

$V_0$, $E_{\frac{1}{2}}$, $DDR_1$ were measured on the resultant photosensitive members in a manner similar to the example 1.

The results are shown in Table 1.

EXAMPLES 29–32

Photosensitive members with the same structure as that of Example 17 were prepared in a manner similar to Example 17 except that the hydrazone compounds(IV-12), (IV-14), (IV-17), (IV-18) were used respectively instead of the hydrazone compound (III-7).

$V_0$, $E_{\frac{1}{2}}$, $DDR_1$ were measured on the resultant photosensitive members in a manner similar to the example 1.

The results are shown in Table 1.

EXAMPLES 33–36

Photosensitive members with the same structure as that of Example 17 were prepared in a manner similar to Example 17 except that the hydrazone compounds(IV-25), (IV-26), (IV-27), (IV-28) were used respectively instead of the hydrazone compound (III-7).

$V_0$, $E_{\frac{1}{2}}$, $DDR_1$ were measured on the resultant photosensitive members in a manner similar to the example 1.

The results are shown in Table 1.

COMPARATIVE EXAMPLES 1–4

Photosensitive members with the same structure as that of Example 9 were prepared in a manner similar to Example 9 except that the hydrazone compounds (D), (E), (F), (G), (H), (I), (J), (K), (L) were used respectively instead of the hydrazone compound (I-14).

$V_0$, $E_{\frac{1}{2}}$, $DDR_1$ were measured on the resultant photosensitive members in a manner similar to the example 1.

The results are shown in Table 1.

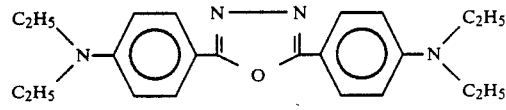

[D]

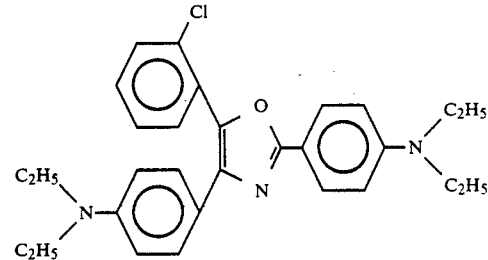

[E]

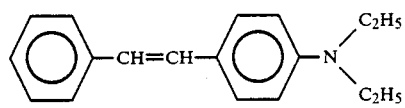

[F]

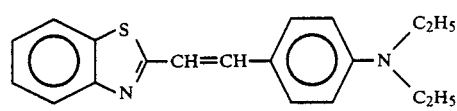

[G]

-continued

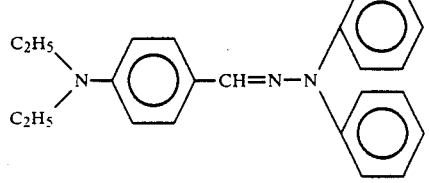
[H]

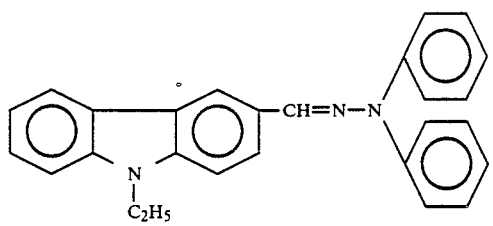
[I]

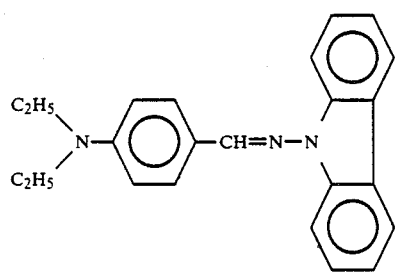
[J]

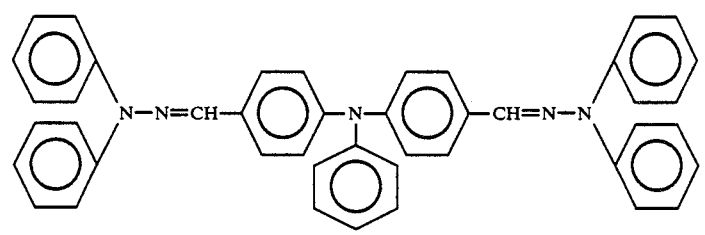
[K]

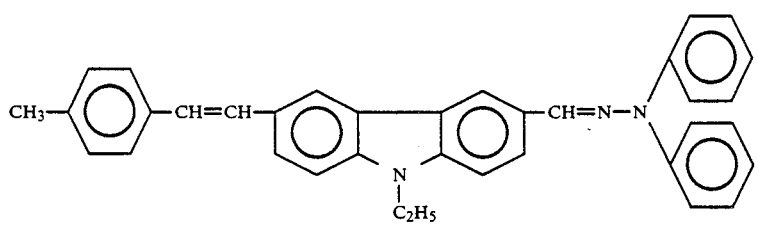
[L]

| TABLE 1 | | | |
|---|---|---|---|
| | $V_o$ (V) | $E_{1/2}$ (lux.sec) | $DDR_1$ (%) |
| Example 1 | −650 | 1.3 | 3.3 |
| Example 2 | −660 | 1.5 | 2.8 |
| Example 3 | −650 | 1.1 | 3.5 |
| Example 4 | −650 | 1.0 | 3.2 |
| Example 5 | −660 | 1.8 | 2.7 |
| Example 6 | −650 | 1.4 | 3.2 |
| Example 7 | −660 | 1.7 | 3.0 |
| Example 8 | −660 | 1.6 | 2.8 |
| Exmaple 9 | +620 | 1.4 | 13.3 |
| Exmaple 10 | +630 | 1.5 | 12.5 |
| Example 11 | +620 | 1.2 | 13.0 |
| Example 12 | +620 | 1.0 | 13.6 |
| Example 13 | −660 | 1.8 | 2.8 |
| Example 14 | −660 | 1.6 | 3.0 |
| Example 15 | −650 | 1.4 | 3.5 |
| Example 16 | −650 | 1.2 | 3.3 |
| Example 17 | −660 | 1.5 | 3.0 |
| Example 18 | −660 | 1.9 | 2.8 |

| TABLE 1-continued | | | |
|---|---|---|---|
| | $V_o$ (V) | $E_{1/2}$ (lux.sec) | $DDR_1$ (%) |
| Example 19 | −650 | 1.6 | 3.6 |
| Example 20 | −660 | 1.3 | 3.1 |
| Example 21 | +620 | 1.7 | 12.8 |
| Example 22 | +620 | 1.5 | 13.2 |
| Example 23 | +610 | 1.2 | 13.5 |
| Exmaple 24 | +600 | 1.0 | 14.0 |
| Example 25 | −660 | 1.3 | 2.7 |
| Example 26 | −650 | 1.2 | 3.1 |
| Example 27 | −660 | 1.6 | 2.8 |
| Example 28 | −660 | 1.5 | 2.7 |
| Example 29 | −660 | 1.8 | 2.8 |
| Example 30 | −660 | 1.7 | 2.6 |
| Example 31 | −650 | 1.4 | 3.2 |
| Example 32 | −650 | 1.2 | 3.5 |
| Example 33 | +620 | 1.3 | 13.2 |
| Example 34 | +610 | 0.9 | 14.0 |
| Example 35 | +610 | 0.8 | 13.7 |
| Example 36 | +620 | 1.0 | 12.9 |

TABLE 1-continued

| | $V_o$ (V) | $E_{\frac{1}{2}}$ (lux.sec) | $DDR_1$ (%) |
|---|---|---|---|
| Comparative Example 1 | +620 | 36.0 | 6.5 |
| Comparative Example 2 | +600 | 5.7 | 14.0 |
| Comparative Example 3 | +610 | 12.8 | 10.8 |
| Comparative Example 4 | +620 | 15.0 | 12.0 |
| Comparative Example 5 | +600 | 3.2 | 14.3 |
| Comparative Example 6 | +610 | 4.7 | 13.2 |
| Comparative Example 7 | +620 | 5.3 | 12.4 |
| Comparative Example 8 | +610 | 2.8 | 12.7 |
| Comparative Example 9 | +610 | 4.5 | 12.9 |

Even though a photosensitive member of the present invention is a monolayer type or a laminated type, it has a sufficient charge keeping ability, and the potential decay rate in the dark is so small that a photosensitive member of the invention can be put into practical use. The photosensitive member of the invention is excellent in sensitivity.

The photosensitive members respectively prepared in the examples 9, 21 and 33 were installed in a commercial copying machine (EP-350Z made by Minolta Camera K.K.) to be subjected to a copying repetition test when charged positively. Even after a copying process was repeated 1000 times in each of the examples 9, 21 and 33, copied images were as clear and excellent in gradient as those of initial copied images. The sensitivity did not change during the repetition test. It is understood that a photosensitive member of the present invention is stable in repetition properties.

What is claimed is:

1. A photosensitive layer formed on or over the substrate and including a charge generating material and a hydrazone compound represented by the general formula (I);

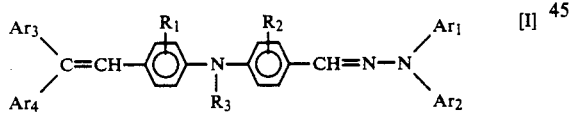

wherein $R_1$ and $R_2$ are independently a hydrogen atom, an alkyl group, an alkoxy group or a halogen atom; $R_3$ is a hydrogen atom, an alkyl group, an aralkyl group, an aryl group, a condensed polycyclic ring group or a heterocyclic ring group (these groups may have one or more substituent(s)); $R_3$ may form a condensed ring together with a benzene ring in the formula (I); $Ar_1$ and $Ar_2$ are independently an alkyl group, an aryl group, a condensed polycyclic ring group or a heterocyclic ring group (these groups may have one or more substituent(s); $Ar_3$ and $Ar_4$ are independently a hydrogen atom, an alkyl group, an aryl group, a condensed polycyclic ring group or a heterocyclic ring group (these groups may have one or more substituent(s); $Ar_3$ and $Ar_4$ are not hydrogen atoms at the same time; $Ar_1$ and $Ar_2$, and/or $Ar_3$ and $Ar_4$ may form a ring in combination.

2. A photosensitive member of claim 1, wherein the hydrazone compound is a charge transporting material.

3. A photosensitive member of claim 1, wherein the photosensitive layer comprises a charge transporting layer and a charge generating layer.

4. A photosensitive member of claim 3, wherein the charge generating layer is 4 μm or less in thickness.

5. A photosensitive member of claim 3, wherein the charge transporting layer is 3-30 μm in thickness.

6. A photosensitive member of claim 3, the charge transporting layer comprises the hydrazone compound dispersed in a resin.

7. A photosensitive member of claim 6, wherein the charge transporting layer contains the hydrazone compound at the content of 0.2-2 parts by weight on the 8. A photosensitive member of claim 6, wherein volume resistance of the resin is $1 \times 10^{12}$ Ω.cm or more.

9. A photosensitive member of claim 1, wherein the photosensitive layer comprises the hydrazone compound and a charge generating material which are dispersed in a resin.

10. A photosensitive member of claim 9, wherein the photosensitive layer is 3-30 μm in thickness.

11. A photosensitive member of claim 9, wherein the photosensitive layer contains the chage genarating material at the content of 0.01-3 parts by weight on the basis of 1 part by weight of the resin.

12. A photosensitive member of claim 9, wherein the photosensitive layer contains the hydrazone compound at the content of 0.2-30 parts by weight on the basis of 1 part by weight of the resin.

13. A potosensitive member of claim 1, wherein a surface protective layer is formed on the photosensitive layer.

14. A photosensitive member of claim 1, wherein an intermediate layer is formed between the electrically conductive substrate and the photosensitive layer.

15. A photosensitive member comprising an electrically conductive substrate; and a photosensitive layer formed on or over the substrate and including a charge generating material and a hydrazone compound represented by the general formula (II);

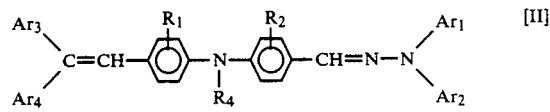

wherein $R_1$ and $R_2$ are independently a hydrogen atom, an alkyl group, an alkoxy group or a halogen atom; $R_4$ is a hydrogen atom, an alkyl group, an aralkyl group, an aryl group, a condensed polycyclic ring group or a heterocyclic ring group (these groups may have one or more substituent(s); $Ar_1$ and $Ar_2$ are independently an alkyl group, an aryl group, a condensed polycyclic ring group or a heterocyclic ring group (these groups may have one or more substituent(s); $Ar_3$ and $Ar_4$ are independently a hydrogen atom, an alkyl group, an aryl group, a condensed polycyclic ring group, a substituent or a heterocyclic ring group (these groups may have one or more substituent(s); $Ar_3$ and $Ar_4$ are not hydrogen atoms at the same time; $Ar_1$ and $Ar_2$, and/or $Ar_3$ and $Ar_4$ may form a ring in combination.

16. A photosensitive member of claim 15, wherein Ar$_1$, Ar$_2$, Ar$_3$ and/or Ar$_4$ are(is) an electon donating group respectively.

17. A photosensitive member of claim 15, wherein Ar$_3$ and Ar$_4$ are a phenyl group respectively.

18. A photosensitive member of claim 15, wherein Ar$_3$ and/or Ar$_4$ have(has) an electron donating substituent respectively.

19. A photosensitive member of claim 18, wherein the substituent is a substituted amino group or an alkoxy group.

20. A photosensitive member comprising an electrically conductive substrate; and
a photosensitive layer formed on or over the substrate and including a charge generating material and a hydrazone compound represented by the general formula (III);

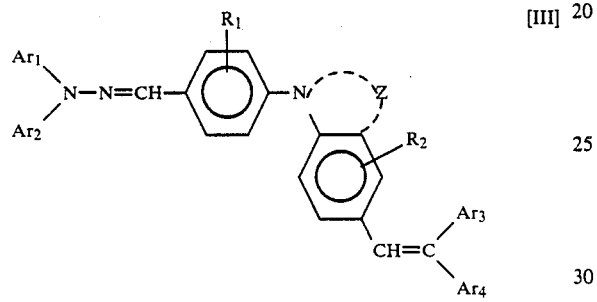

wherein R$_1$ and R$_2$ are independently a hydrogen atom, an alkyl group, an alkoxy group or a halogen atom; Z is a residual group forming a condensed ring group together with a benzene ring in the formula (III); Ar$_1$ and Ar$_2$ are independently an alkyl group, an aryl group, a condensed polycyclic ring group or a heterocyclic ring group (these groups may have one or more substituent(s); Ar$_3$ and Ar$_4$ are independently a hydrogen atom, an alkyl group, an aryl group, a condensed polycyclic ring group or a heterocyclic ring group (these groups may have one or more substituent(s); Ar$_3$ and Ar$_4$ are not hydrogen atoms at the same time; Ar$_1$ and Ar$_2$, and/or Ar$_3$ and Ar$_4$ may form a ring in combination.

21. A photosensitive member of claim 20, wherein Ar$_1$, Ar$_2$, Ar$_3$ and/or Ar$_4$ are(is) an electon donating group respectively.

22. A photosensitive member of claim 20, wherein Ar$_3$ and Ar$_4$ are a phenyl group respectively.

23. A photosensitive member of claim 20, wherein Ar$_3$ and/or Ar$_4$ have(has) an electron donating substituent respectively.

24. A photosensitive member of claim 23, wherein the substituent is a substituted amino group or an alkoxy group.

25. A photosensitive member comprising an electrically conductive substrate; and
a photosensitive layer formed on or over the substrate and including a charge generating material and a hydrazone compound represented by the general formula (IV);

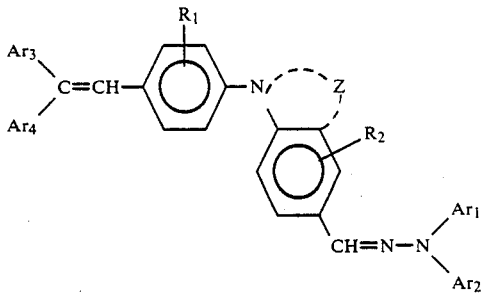

wherein R$_1$ and R$_2$ are independently a hydrogen atom, an alkyl group, an alkoxy group or a halogen atom; Z is a residual group forming a condensed ring together with a benzene ring in the formula (IV); Ar$_1$ and Ar$_2$ are independently an alkyl group, an aryl group, a condensed polycyclic ring group or a heterocyclic ring group (these groups may have one or more substituent(s); Ar$_3$ and Ar$_4$ are independently a hydrogen atom, an alkyl group, an aryl group, a condensed polycyclic ring group or a heterocyclic ring group these groups may have one or more substituent(s); Ar$_3$ and Ar$_4$ are not hydrogen atoms at the same time; Ar$_1$ and Ar$_2$, and/or Ar$_3$ and Ar$_4$ may form a ring in combination.

26. A photosensitive member of claim 25, wherein Ar$_1$, Ar$_2$, Ar$_3$ and/or Ar$_4$ are(is) an electon donating group respectively.

27. A photosensitive member of claim 25, wherein Ar$_3$ and Ar$_4$ are a phenyl group respectively.

28. A photosensitive member of claim 25, wherein Ar$_3$ and/or Ar$_4$ have(has) an electron donating substituent respectively.

29. A photosensitive member of claim 28, wherein the substituent is a substituted amino group or an alkoxy group.

* * * * *